United States Patent [19]
Sun et al.

[11] Patent Number: 6,042,845
[45] Date of Patent: *Mar. 28, 2000

[54] ANTI FUNGAL TREATMENT OF NAILS

[75] Inventors: Ying Sun, Somerville; Jue-Chen Liu, Neshanic; Elizabeth S. Kimbleton, Princeton; Jonas C. T. Wang, Robbinsville, all of N.J.

[73] Assignee: Johnson & Johnson Consumer Products, Inc., Skillman, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/922,041

[22] Filed: Sep. 2, 1997

Related U.S. Application Data

[63] Continuation of application No. 08/361,413, Dec. 22, 1994, Pat. No. 5,696,164.

[51] Int. Cl.⁷ ........................................................ A61L 15/16
[52] U.S. Cl. ........................... 424/446; 424/447; 424/448; 514/562; 514/946; 514/947; 514/953; 514/252
[58] Field of Search ....................................... 514/252, 562, 514/588, 946, 947, 953, 399; 424/446, 447, 448

Primary Examiner—Samuel Barts

[57] ABSTRACT

There is disclosed a method for the treatment of fungal diseases in nails, which comprises the topical administration to the nail and, if desired, also to the surrounding skin, of (1) a sulfhydryl containing amino acid or a derivative thereof, the pharmaceutically acceptable salts or esters thereof, or stereoisomers thereof, (2) urea, (1) and (2) being administered in an amount sufficient to enhance the permeation of antifungal drugs through nail tissue, either prior to or, preferably, concurrently with the topical administration to the nail of (3) an effective amount of an antifungal drug. There is also disclosed a bandage adapted for the topical administration of medication to the nail, said bandage comprising a T-shaped adhesive backing, and a flexible pad having an impervious backing and a nail-shaped cavity backed by said impervious backing, wherein said nail-shaped cavity contains absorptive means having absorbed therein urea and a sulfhydryl containing amino acid or a derivative thereof, a pharmaceutically acceptable salt or ester thereof, or a stereoisomer thereof.

5 Claims, 17 Drawing Sheets

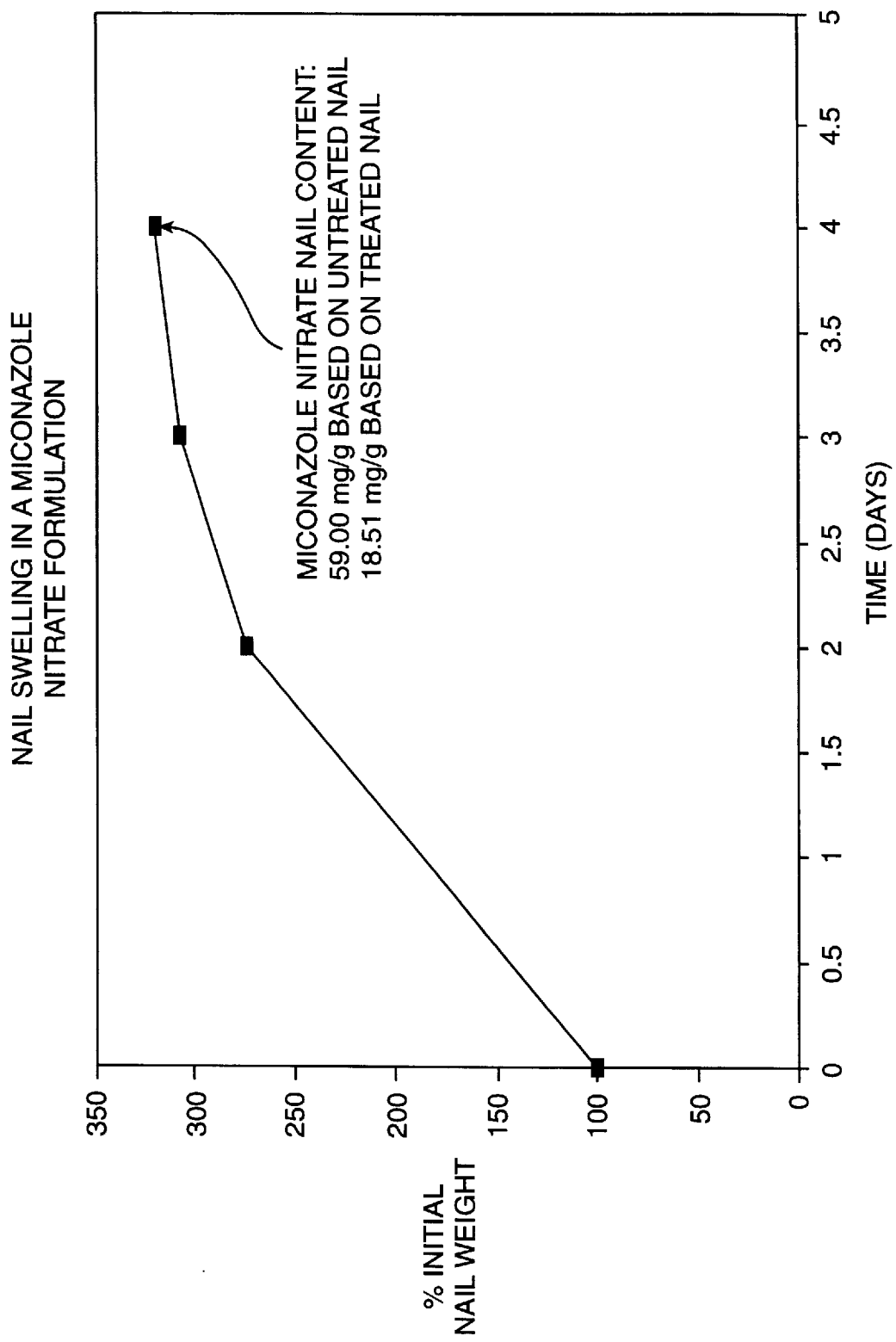

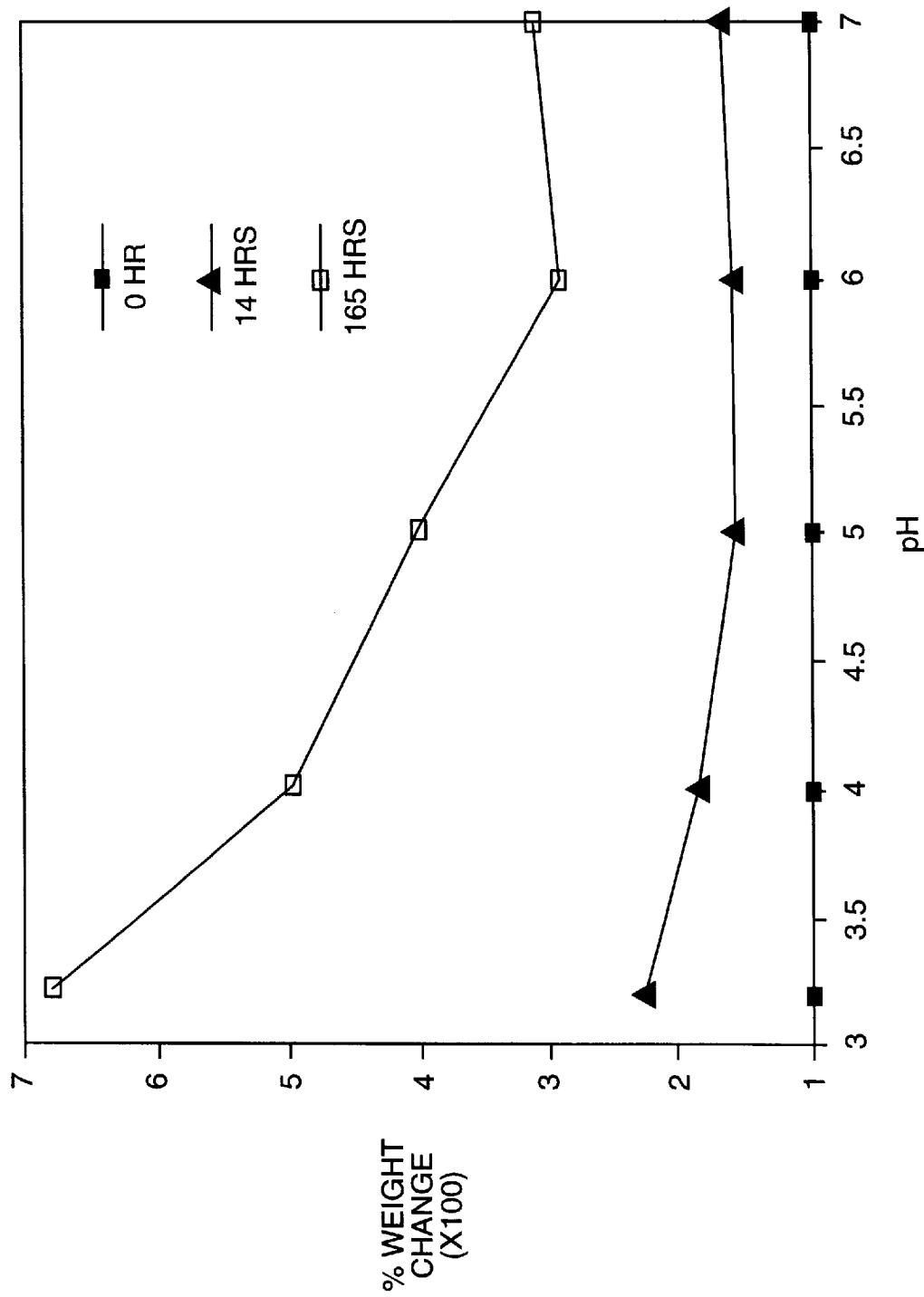

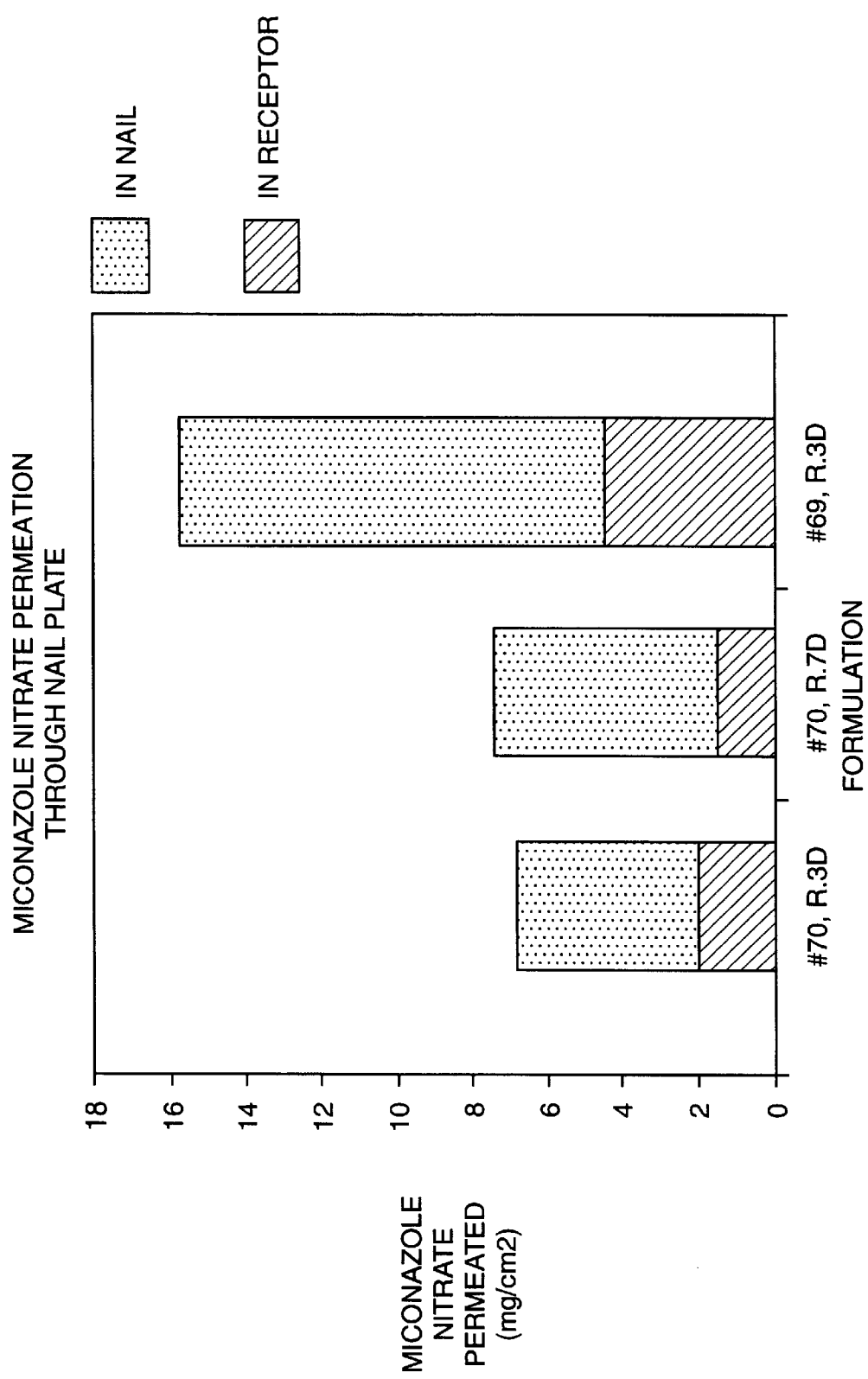

ANTI FUNGAL TREATMENT OF NAILS

This is a continuation, of application Ser. No. 08/361,413, filed Dec. 22, 1994, which is hereby incorporated by reference now U.S. Pat. No. 5,696,164.

The invention relates to a method for the topical treatment of fungal diseases in nails, and more particularly, to a composition and a method for enhancing the permeation rate of antifungal agents in nails. The invention also relates to a bandage adapted for use with the method of the invention.

BACKGROUND OF THE INVENTION

Although significant progress has been made in the development of antifungal drugs, nail fungal infection (e.g., onychomycosis) remains a disease most difficult to treat. The target sites for the treatment of onychomycosis reside in the nail plate, nail bed and nail matrix (see FIG. 1). Topical treatment has not been effective because antifungal drugs cannot readily penetrate the nail plate to reach the infection sites under the nail. Oral administration of antifungal drugs is the only effective way to treat onychomycosis, which has limited the use of some of the more potent antifungal drugs such as itraconazole and ketoconazole because of concern for possible side effects. It has been shown, however, that if the nail barrier can be overcome or eliminated, topical antifungal drug treatment can be effective. For example, both miconazole and ketoconazole were demonstrated to be effective in topically treating onychomycosis after nail avulsion. There is a need for a methodology for topical nail fungal treatment that does not require removal of the nail. Such topical treatment would then permit the use of the more potent antifungal drugs in the treatment of fungal-infected nails.

The nail plate is too thick and too dense for drugs to penetrate at a practical rate. Although nail is similar to stratum corneum of the skin in that it is derived from epidermis, it is mainly composed of hard keratin (highly disulfide-linked) and is approximately 100-fold thicker than stratum corneum. In order to deliver a sufficient amount of drug into the nail plate, the permeability of the nail plate to the drug needs to be enhanced. The permeation-related properties of the nail differ from those observed in stratum corneum primarily in three respects: (a) the total lipid content of the nail is much less than the lipid content of stratum corneum; (b) the nail has a high sulphur content (cystine) in its hard keratin domain whereas the stratum corneum does not; (c) under average conditions, the nail contains much less water than the stratum corneum.

The chemical composition of nail and experimental evidence indicate that the aqueous pathway plays a dominant role in drug penetration into nail. Water is the principal plasticizer for the nail. Upon being hydrated, hard nail plates become softer and more flexible. Nail hydration is influenced by many factors, such as solution pH and certain chemicals. Keratolytic agents, such as urea and salicylic acid are often used to soften nail plates. Urea and a combination of urea and salicylic acid were reported to be used for nonsurgical avulsion of nail dystrophies in clinical studies prior to topical treatment of onychomycosis with satisfactory results.

Nail plates have high sulphur content in the form of disulfide bonds. Certain reducing agents, e.g., cysteine or a derivative thereof, can break the disulfide bond in keratin to increase the ability of the nail to hydrate. The chemical reaction that occurs between the disulfide bonds in nail keratin and a thiol-containing compound (in this case, cysteine) is shown in the following scheme:

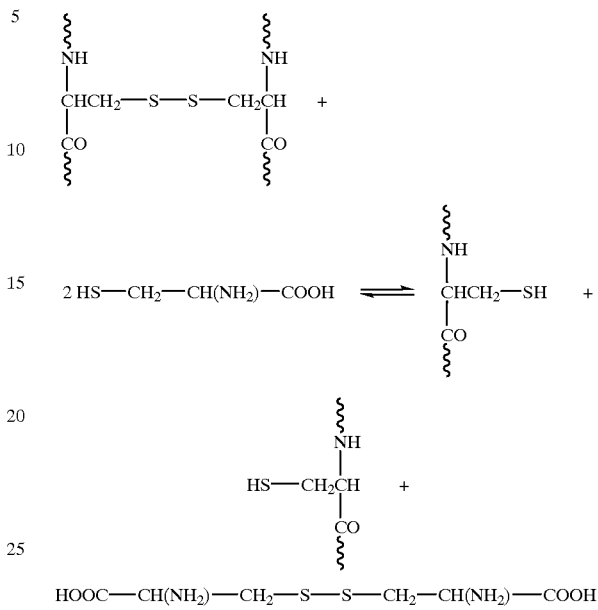

This invention provides a delivery means for topical treatment of fungal diseases of the nail which delivers an effective dose of drug to (a) the diseased nail plate (and consequently, the underlying nail bed), of which the hydration capability has been significantly increased to enhance drug permeability (nail route); and (b) the surrounding skin tissues, including nail bed and matrix via the eponychium and hyponychium (skin route—see FIG. 1).

BRIEF SUMMARY OF THE INVENTION

The invention provides a method for the treatment of fungal diseases in nails, which comprises the topical administration to the nail and, if desired, also to the surrounding skin, of (1) a sulfhydryl containing amino acid or a derivative thereof, the pharmaceutically acceptable salts or esters thereof, or stereoisomers thereof, (2) urea, (1) and (2) being administered in an amount sufficient to enhance the permeation of antifungal drugs through nail tissue, either prior to or, preferably, concurrently with the topical administration to the nail of (3) an effective amount of an antifungal drug. The invention also provides a composition comprising (1), (2) and (3), as described above.

The invention further provides a bandage adapted for the topical administration of medication to the nail, said bandage comprising a T-shaped adhesive backing, and a flexible pad having an impervious backing and a nail-shaped cavity backed by said impervious backing, wherein said nail-shaped cavity contains absorptive means having absorbed therein urea and a sulfhydryl containing amino acid or a derivative thereof, a pharmaceutically acceptable salt or ester thereof, or a stereoisomer thereof.

THE PRIOR ART

The reduction reaction between keratin disulfide bonds and thioglycolates are frequently utilized in the cosmetic industry, e.g., for cold waving and depilatory of hair, and enhancing cosmetic appearance of the nail.

Olthoff et al., in EP 440298 A1, disclose the use of sulfur-containing amino acid derivatives in topical preparations for treatment of nail diseases such as onychomycosis.

Kawase et al (EP 472858 A2 Mar. 4, 1992) describe a hair treatment composition containing siloxanes and penetration enhancers such as ammonium thioglycolate, which gives the treated hair a good gloss and a reduced number of hair splits.

Puri (WO 8600013 A1 Jan. 3, 1986) discloses that the condition of hair, skin and nails is improved by treatment with an aqueous ammonium thioglycolate solution, followed by treatment with a protein hydrolyzate.

Rothman (WO 8907930 A1 Sep. 8, 1989) describes a storage-stable protein-containing composition and a method for treating keratinous tissues. The protein-containing composition contains reducing agents such as ammonium thioglycolate. The composition is said to be useful for conditioning horny keratinous tissues of mammals such as human hair and nail, and the hooves and fur of animals, to improve their strength and appearance and to promote hair and nail growth.

An enhanced transdermal drug permeation in rats has been reported for theophylline [K. Kushida et al., Chem. Pharm. Bull., 32, 1 (1984) 268–274] and insulin [Y. Sun et al., Ann. New York Academy of Sciences, 1990, 596; Y. Sun et al., Proceed. Intern. Sym. Control. Rel. Bioactive Mat., 17 (1990) 202; and J. C. Liu et al., in *Drug Permeation Enhancement: Theory and Applications*, p247–272, (D. S. Hsieh, Ed.) Marcel Dekker, Inc., 1994] by pretreating the skin with aqueous calcium thioglycolate solution. On the other hand, direct addition of calcium thioglycolate into an ointment containing the calcium salt of indomethacin dramatically decreased the absorption of the drug [T. Ogiso et al., J. Pharmcobio-Dyn., 9 (1986) 517–525].

Konno et. al. (EP 152281 A2 Aug. 21, 1985) describes a transdermal formulation of nicardipine hydrochloride containing urea and thioglycol.

BRIEF DESCRIPTION OF THE DRAWINGS

FIG. 7 is a graph showing nail swelling and miconazcle nitrate partitioning into nail in a miconazole nitrate cream formulation;

FIG. 8 is a graph showing the nail swelling—pH profile with nail clippings immersed in a formulation containing urea, propylene carbonate, propylene glycol, N-acetyl-1-cysteine and water, at differing pH values;

FIG. 12 is a graph that shows the amount of miconazole nitrate penetrated through the nail plate, as well as the amount retained in the nail plate, for three formulations.

DETAILED DESCRIPTION OF THE INVENTION

The invention relates to a method for the treatment of fungal diseases in nails, which comprises the topical administration to the nail of (1) a sulfhydryl containing amino acid or a derivative thereof, the pharmaceutically acceptable salts or esters thereof, or stereoisomers thereof, (2) urea, (1) and (2) being administered in an amount sufficient to enhance the permeation of antifungal drugs through nail tissue, either prior to or, preferably, concurrently with the topical administration to the nail of (3) an effective amount of an antifungal drug.

Figure 1:
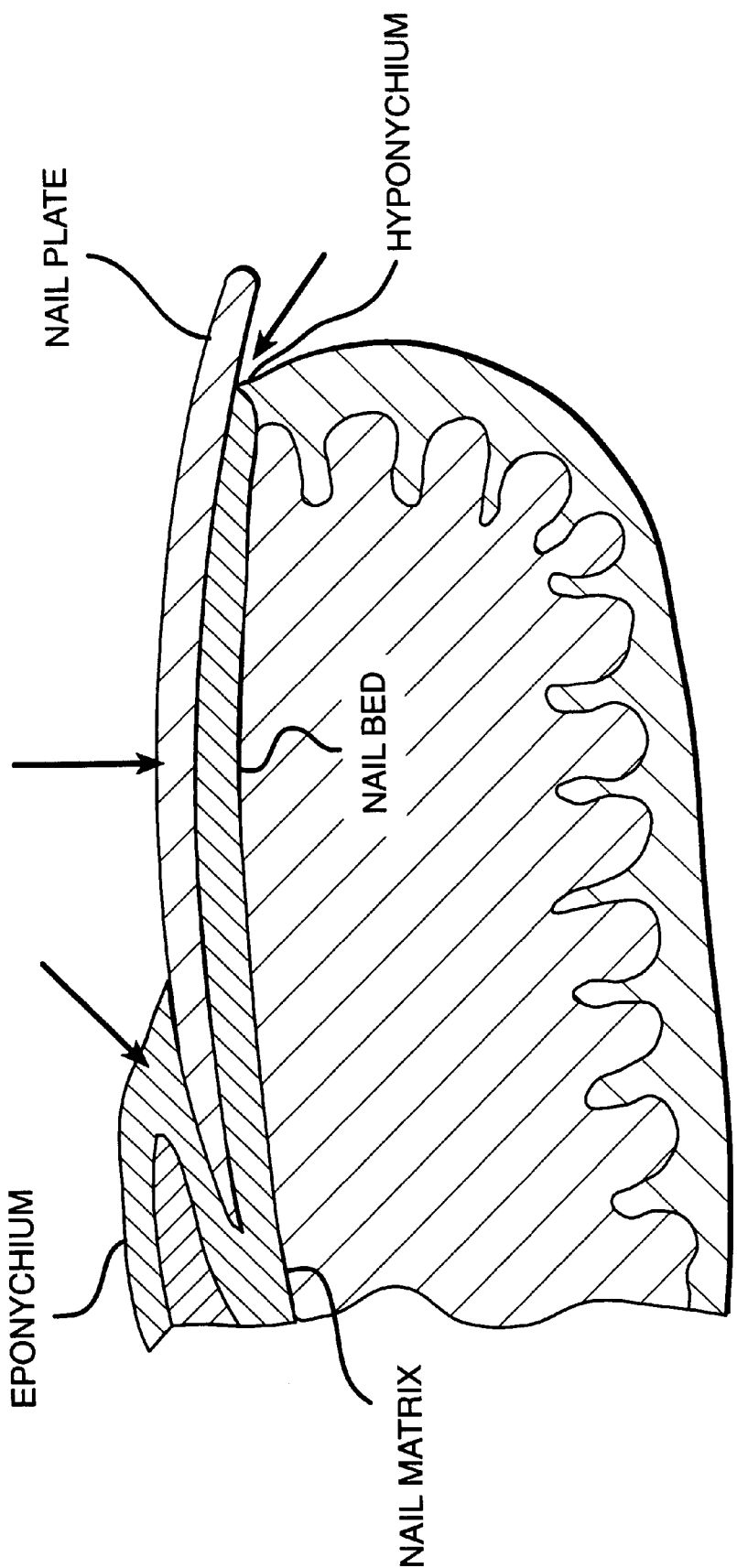
FIG. 1 shows the treatment target sites of a fungus-infected nail.

The term "nail" means the horny cutaneous plate on the dorsal surface of the distal end of a finger or toe. FIG. 1 is a schematic diagram showing the basic anatomic structure of human nail and its surrounding tissues. The topical antifungal drug treatment for nail fungal disease (onychomycosis) contemplated by this invention is intended to deliver antifungal drug to the nail plate (the stratum corneum unguis) and to the nail bed (the modified area of epidermis beneath the nail, over which the nail plate slides as it grows) through the nail plate. Desirably, antifungal drug is also concurrently administered to the nail matrix (the proximal portion of the nail bed from which growth chiefly proceeds) and nail bed through the skin of the eponychium (commonly called the cuticle) and the hyponychium (the thickened epidermis underneath the free distal end of the nail).

The topical treatment of the invention may be employed in combination with systemic treatment with an antifungal drug such as griseofulvin or other antifungal drug that can be given orally over long periods of time, either concurrently during the entire systemic treatment regimen, or concurrently during a portion (usually the latter phase) of the systemic treatment regimen, or following such systemic treatment.

The fungal diseases of the nail that can be treated in accordance with the invention are those that are called "onychomycosis", which is usually an infection by *Epidermophyton floccosum*, several species of Trichophyton, or *Candida albicans*.

The antifungal drugs that can be used in the invention include miconazole nitrate, ketoconazole, itraconazole, fluconazole, econazole, terconazole, saperconazole, amorolfine, ciclopirox, oxiconazole, clotrimazole, terbinafine, naftifine, and other antifungal drugs that are available in a topical formulation. The preferred antifungal drugs for use in the process of the invention are itraconazole, ketoconazole and miconazole nitrate. If desired, the topical formulation containing the antifungal drug may include an agent such as hydroxypropyl-β-cyclodextrin that enhances the water-solubility of the antifungal drug, in order to better utilize the aqueous pathway through the nail, as discussed above. The anti-fungal drugs are used in anti-fungally effective amounts. For example, anti-fungally effective amounts are usually from about 0.5% to about 10%, by weight, and preferably from about 1% to about 5%, by weight, of the formulation that is applied to the nail or surrounding dermal tissue.

Urea is employed in the invention. It is believed that urea's principal contribution to the efficacy of the formulation used in the invention is to inhibit the nail keratin from returning to its original densely packed cross-linked state (such return to the original densely packed cross-linked state would be caused by oxidation from the oxygen in the atmosphere), so that the nail remains more permeable to the antifungal drug over a longer period of time. (The ability of urea to inhibit the nail keratin from returning to its original densely packed cross-linked state probably stems from urea's ability to disrupt non-covalent interactions in nail keratin.) One beneficial effect of the use of urea is that the sulfhydryl-containing amino acid or derivative thereof can be used in a lower concentration, thereby reducing (although probably not eliminating) the potential of the amino acid or derivative thereof for irritation of the skin.

The invention employs a sulfhydryl containing amino acid or a derivative thereof, the pharmaceutically acceptable salts or esters thereof, or stereoisomers thereof. Such compounds can be represented by Formula (I):

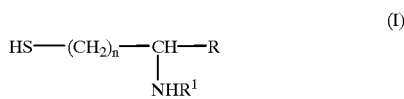

(I)

the pharmaceutically acceptable salts or esters thereof, and stereoisomers thereof, wherein:
R=H, CONHCH$_2$COOH, NH$_2$ or COOR$^2$ wherein R$^2$ is H or C$_{1-4}$alkyl;
R$^1$=H, COCH$_3$, CONH$_2$, or CO(CH$_2$)$_m$CH(NH$_2$)(COOH) wherein m is 1 or 2; and
n=a number having a value of from 1 to 4.

Illustrative examples of compounds of Formula (I) include those shown in the following table:

TABLE 1

Cysteine (1-cysteine, d-cysteine, dl-cysteine)

HS—CH$_2$—CH(NH$_2$)—COOH

N-Acetyl-1-cysteine

HS—CH$_2$—CH(NH-COCH$_3$)—COOH dl-Homocysteine

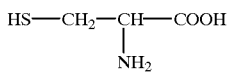

1-Cysteine methyl ester (methyl cysteine)

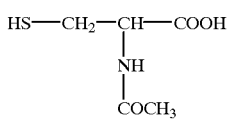

TABLE 1-continued

1-Cysteine ethyl ester (ethyl cysteine)

HS—CH$_2$—CH(NH$_2$)—COOCH$_2$CH$_3$

N-Carbamoyl cysteine

HS—CH$_2$—CH(NH-CO-NH$_2$)—COOH

Glutathione

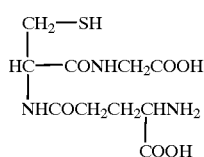

Cysteamine

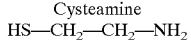

The preferred compounds for use in the invention are N-acetyl-1-cysteine and cysteine.

The urea and the sulfhydryl-containing amino acid or derivative thereof are employed in amounts sufficient to enhance the permeation of antifungal drugs through nail tissue. Thus, the topical composition that is applied to the nail will ordinarily contains from about 1% to about 50%, and preferably from about 5% to about 20%, (by weight) urea, and from about 0.1% to about 40%, and preferably from about 3% to about 20%, (by weight) of the sulfhydryl-containing amino acid or derivative thereof, the percentages being based upon the total weight of the formulation being applied to the nail. The pH range of the formulation is usually from about pH 2 to pH 10, and preferably from about pH 3 to pH 8.

EXPERIMENTAL a. Effect of Nail Penetration Enhancers on Nail Swelling and Drug Partitioning into Nail The ability of a drug in a formulation to penetrate nail plate should be reflected by the rate and extent of the nail uptake of the formulation (i.e., nail swelling in the formulation), as well as by the amount of the drug migration into the nail (drug partitioning into nail). In vitro experiments were conducted to examine the effect of drug formulation containing nail penetration enhancer on nail swelling and drug partitioning.

The experimental procedure was the following: Clean human nail clippings were equilibrated to a constant weight by placing them in a desiccator over saturated CaCl$_2$·6H$_2$O solution (29% relative humidity at room temperature) for at least 48 hours before use. Approximately 30 mg of human nail clippings were weighed into a glass vial. The exact initial weight was recorded. Four grams of the test formulation (pre-warmed to 32° C.) was added into the vial and maintained at 32° C. under stirring in a Heating/Stirring Module (Reacti-Therm III, Pierce). The changes in nail weights were monitored at predetermined intervals over 48 hours. At the end of the swelling experiment, the nail sample was rinsed with a mixture of N,N-dimethylformamide and methanol (1:1) to remove surface-bound drug. The nail sample was then digested, and the drug concentration in nail was determined by high pressure liquid chromatography method as described by Badcock and Davies, Assay of itraconazole in nail clippings by reversed phase, high performance liquid chromatography, Ann. Clin. Biochem, 27 (1990) 506–508.

Several terms were used to describe the data. The nail swelling was expressed by the percentage of the initial nail weight (i.e., 100% of the initial nail weight means no swelling, and 200% means a nail swelling doubling the original weight, etc). An enhancement factor is used to show the increase in nail swelling due to the presence of nail penetration enhancer in comparison to the control, which were calculated according to the formula: enhancement factor=(% weight gain of the test nail sample)/(% weight gain of control nail sample, i.e., no enhancer & urea in the formulation). Similarly, the enhancement factor for the enhanced itraconazole partitioning into nail is defined as: enhancement factor=(drug concentration in the test nail sample)/(drug concentration in the control nail sample). The drug concentration in nail was calculated by dividing the amount of the drug in nail (mg) by the weight of the initial nail clipping (i.e., dry nail weight in gram). This expression of drug nail concentration is used herein unless specified otherwise.

Figure 2:
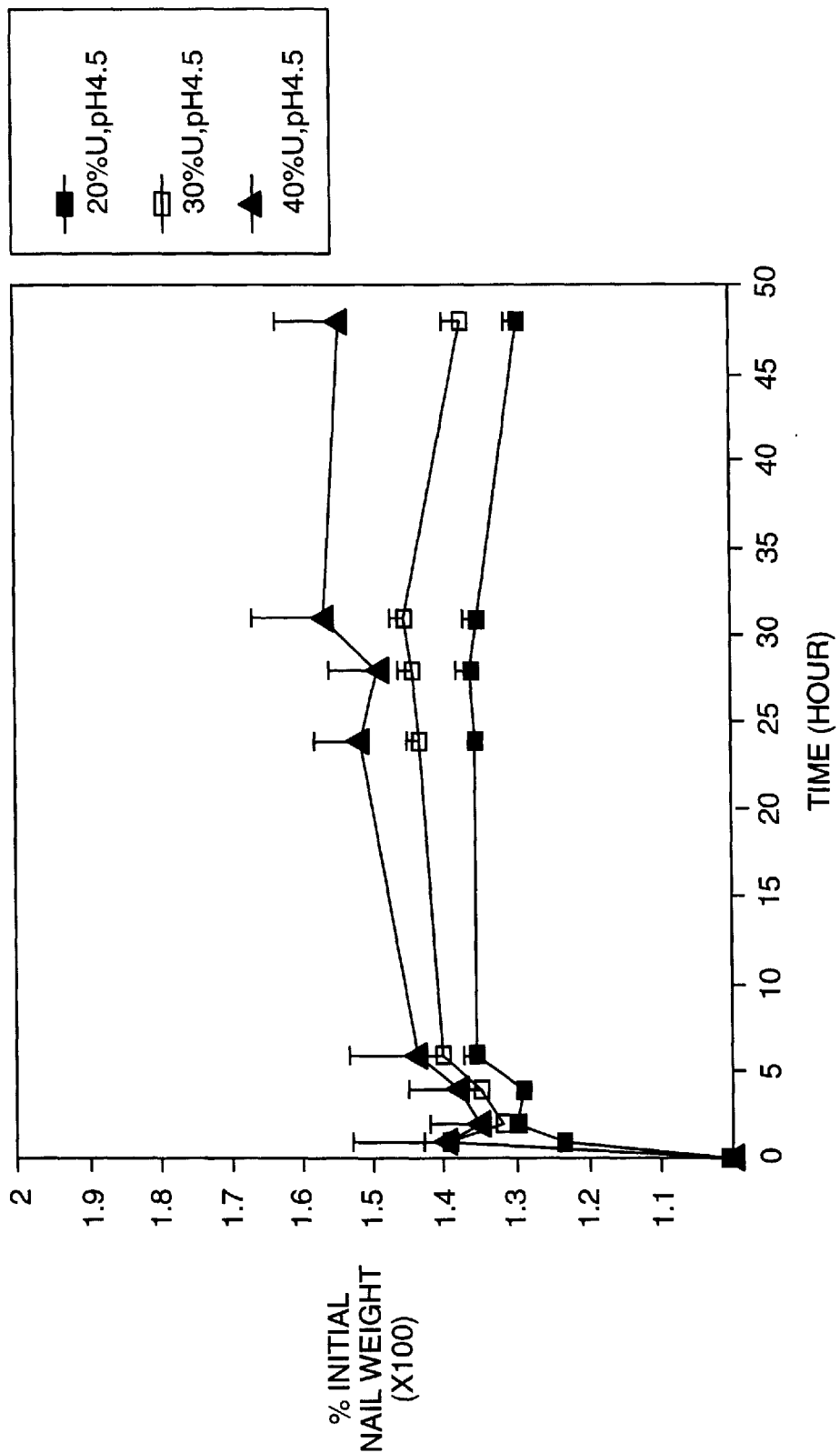
FIG. 2 is a graph displaying the effect of area on nail swelling using aqueous urea solutions of various concentrations at pH 4.5.

The effect of urea on nail swelling was investigated, using aqueous urea solutions of various concentrations at pH 4.5. The graph shown as FIG. 2 shows that as urea concentration increased from 20% to 40%, nail hydration increased from 30% to 50%. For this reason, it is believed that the use of urea alone will not cause significant enhancement of drug permeation through the nail.

TABLE 1, above, shows the names and chemical structures of the thiol-containing amino acids and derivatives thereof that were investigated. To examine the effects of these nail penetration enhancers on nail swelling and drug partitioning, several itraconazole and miconazole nitrate formulations were prepared with an enhancer in each formulation (TABLE 2, below, displays the formulations). In the control experiment, there was no penetration enhancer ("E") or urea ("U") in the formulation. In the experiments discussed below, the following abbreviations and compounds were used:

Ac Cyst=N-acetyl-1-cysteine
Cysteine=1-cysteine
Homocyst=d1-homocysteine
Cysteam=cysteamine
MethylCy=1-cysteine methyl ester
EthylCyst=1-cysteine ethyl ester
Itra=itraconazole
Repl:nd=replenished every n days
SA=salicylic acid (keratolytic agent; pH control)
PG=propylene glycol (solvent)
PC=propylene carbonate (solvent)
EDTA=ethylenediamine tetraacetic acid (disodium salt—chelating agent)
KLUCEL=hydroxypropylcellulose (thickener)
BHT=butylated hydroxy toluene (anti-oxidant)
Mic.Nit.=miconazole nitrate
BHA=Butylated hydroxyanisole
Labrifil M 1944 CS=Unsaturated polyglycolized glycerides obtained by partial alcoholysis of apricot kernel oil, consisting of glycerides and polyethylene glycol esters—an amphiphilic oil, solvent and/or emulsifier.
TEFOSE 63=Ethylene glycol and polyoxyethylene glycol palmitostearate; CTFA adopted name is PEG 6 stearate (and) PEG-32 stearate (and) glycol stearate—a non-ionic self-emulsifying base for oil/water emulsioned preparations.

TABLE 2

| FORMULATIONS | | IN WEIGHT % | | | | | | | | | | |
|---|---|---|---|---|---|---|---|---|---|---|---|---|
| ENHANCER | | ITRA | ENHANCER | SA | UREA | PC | PG | EDTA | BHT | KLUCEL | $H_2O$ | TOTAL |
| No E&U | 8054-40-5 | 1 | 0 | 0 | 0 | 35 | 14 | 0.1 | 0.05 | 0 | 47.85 | 98 |
| Ac Cyst | 8054-33-3 | 1 | 5 | 5 | 10 | 35 | 14 | 0.1 | 0.05 | 0 | 27.85 | 98 |
| Cysteine | 8054-34-1 | 1 | 5 | 5 | 10 | 35 | 14 | 0.1 | 0.05 | 0 | 27.85 | 98 |
| Homocyst | 8054-34-2 | 1 | 5 | 5 | 10 | 35 | 14 | 0.1 | 0.05 | 0 | 27.85 | 98 |
| Cysteam | 8054-34-3 | 1 | 5 | 5 | 10 | 35 | 14 | 0.1 | 0.05 | 0 | 27.85 | 98 |
| MethylCy | 8054-34-4 | 1 | 5 | 5 | 10 | 35 | 14 | 0.1 | 0.05 | 0 | 27.85 | 98 |
| EthylCys | 8054-34-5 | 1 | 5 | 5 | 10 | 35 | 14 | 0.1 | 0.05 | 0 | 27.85 | 98 |
| No Ac&U | 8054-40-1 | 1 | 0 | 0 | 0 | 35 | 10 | 0.1 | 0.05 | 0 | 51.85 | 98 |
| No Ac | 8054-40-2 | 1 | 0 | 0 | 20 | 35 | 10 | 0.1 | 0.05 | 0 | 31.85 | 98 |
| No U | 8054-40-3 | 1 | 5 | 0 | 0 | 35 | 10 | 0.1 | 0.05 | 0 | 46.85 | 98 |
| Ac-#23 | 8054-23 | 1 | 5 | 0 | 20 | 35 | 10 | 0.1 | 0.05 | 0 | 26.85 | 98 |
| No Ac&U | 8054-40-4 | 1 | 0 | 0 | 0 | 35 | 16.5 | 0.1 | 0.05 | 0 | 45.35 | 98 |
| % No Ac | 8054-33-1 | 1 | 0 | 5 | 10 | 35 | 16.5 | 0.1 | 0.05 | 0 | 30.35 | 98 |
| No U | 8054-33-2 | 1 | 5 | 5 | 0 | 35 | 16.5 | 0.1 | 0.05 | 0 | 35.35 | 98 |
| Ac-#26 | 8054-26 | 1 | 5 | 5 | 10 | 35 | 16.5 | 0.1 | 0.05 | 0 | 25.35 | 98 |
| No Ac&U | 8054-40-5 | 1 | 0 | 0 | 0 | 35 | 14 | 0.1 | 0.05 | 0 | 47.85 | 98 |
| No Ac | 8054-33-4 | 1 | 0 | 5 | 10 | 35 | 14 | 0.1 | 0.05 | 0 | 32.85 | 98 |
| No U | 8054-33-5 | 1 | 5 | 5 | 0 | 35 | 14 | 0.1 | 0.05 | 0 | 37.85 | 98 |
| Ac-#33-3 | 8054-33-3 | 1 | 5 | 5 | 10 | 35 | 14 | 0.1 | 0.05 | 0 | 27.85 | 98 |
| ITRACONAZOLE NAIL PERMEATION | | | | | | | | | | | | |
| Repl:3d | 2138-41 | 0.5 | 10 | 0 | 20 | 35 | 10 | 0.1 | 0.05 | 0 | 24.35* | 100 |
| Repl:1d | 2138-136 | 1 | 5 | 0 | 20 | 35 | 10 | 0.1 | 0.05 | 2 | 26.85 | 100 |
| Repl:1d | 2138-137 | 1 | 1 | 0 | 20 | 35 | 10 | 0.1 | 0.05 | 2 | 30.85 | 100 |

TABLE 2-continued

| FORMULATIONS | | IN WEIGHT % | | | | | | | | | |
|---|---|---|---|---|---|---|---|---|---|---|---|
| ENHANCER | ITRA | ENHANCER | SA | UREA | PC | PG | EDTA | BHT | KLUCEL | $H_2O$ | TOTAL |
| MICONAZOLE NITRATE NAIL PERMEATION | | | | | | | | | | | |
| Repl:3d 2138-69 | 2 | 10 | 0 | 20 | 35 | 10 | 0.1 | 0 | 0 | 22.9 | 100 |
| Repl:3d 2138-70 | 2 | 5 | 0 | 20 | 35 | 10 | 0.1 | 0 | 0 | 27.9 | 100 |
| Repl:7d 2138-70 | 2 | 5 | 0 | 20 | 35 | 10 | 0.1 | 0 | 0 | 27.9 | 100 |

*Includes 0.1% ascorbic acid.

Figure 3A:
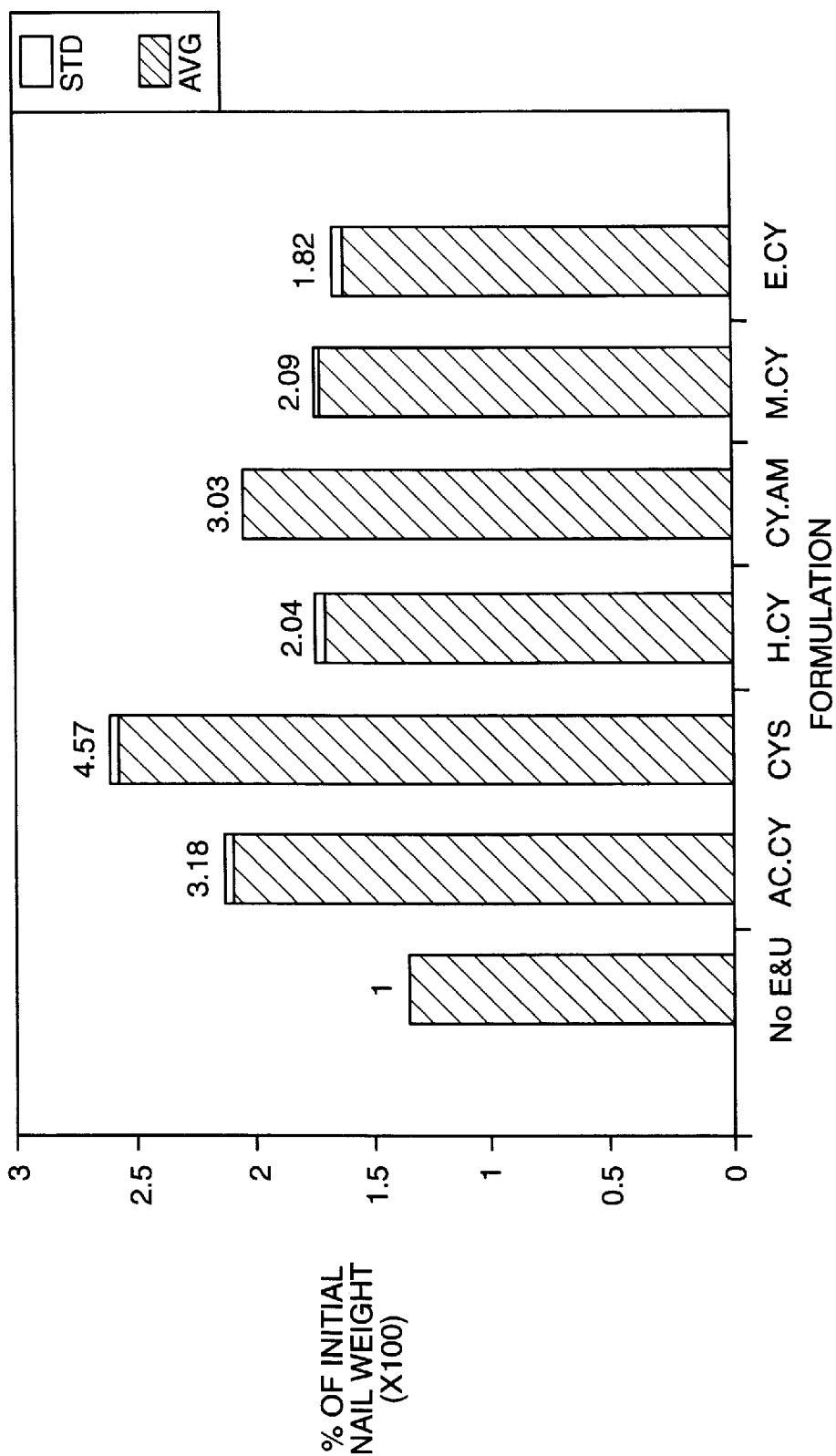
FIG. 3a is a graph showing comparisons of the nail swelling enhancement among several thiol-containing amino acid and analogs after nail clippings were immersed in the formulation at 32° C. for 48 hours.
Figure 3B:
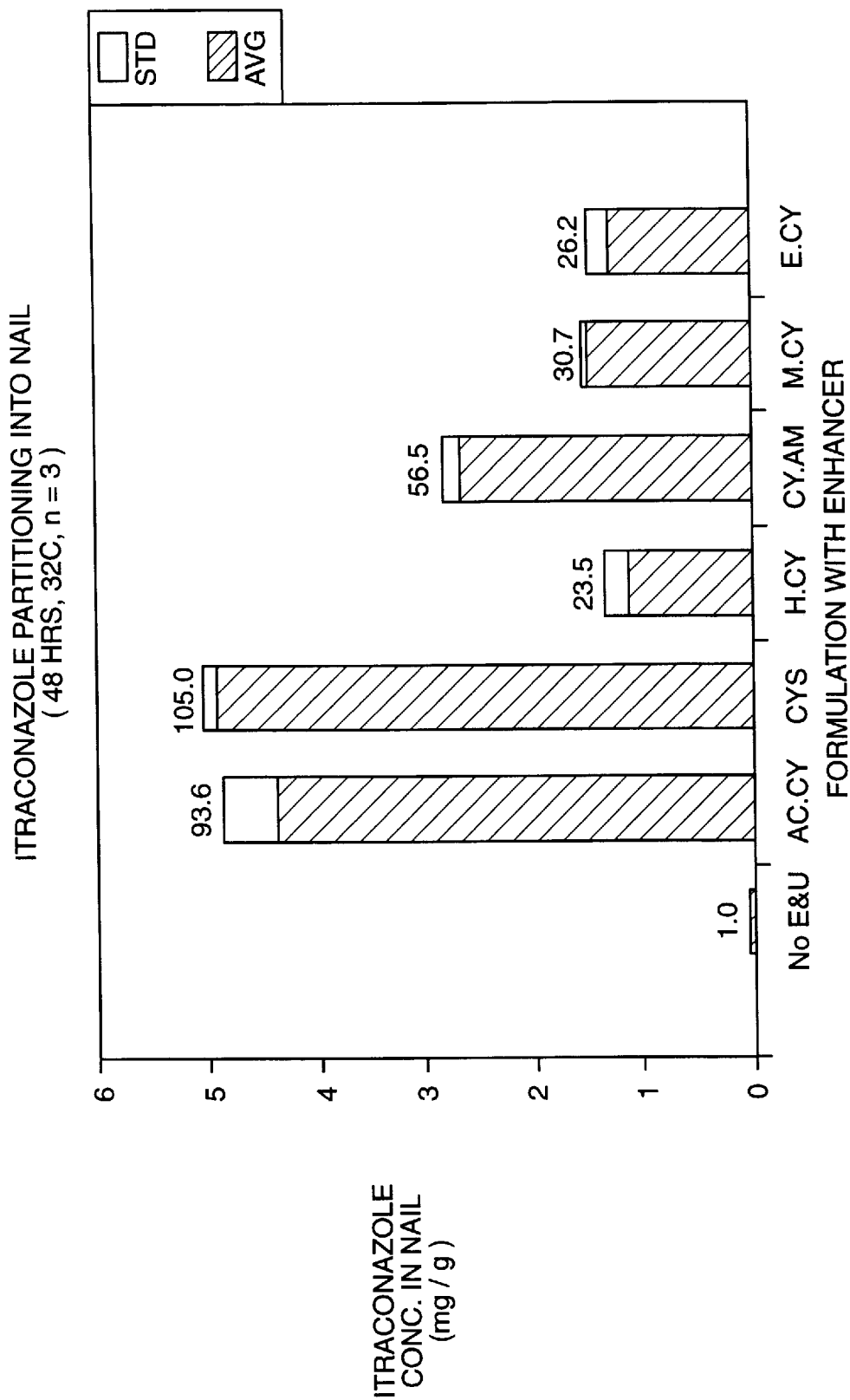
FIG. 3b is a graph showing comparisons of the partitioning of itraconazole into nail among several thiol-containing amino acid and analogs after nail clippings were immersed in the formulation at 32° C. for 48 hours.
Figure 4A:
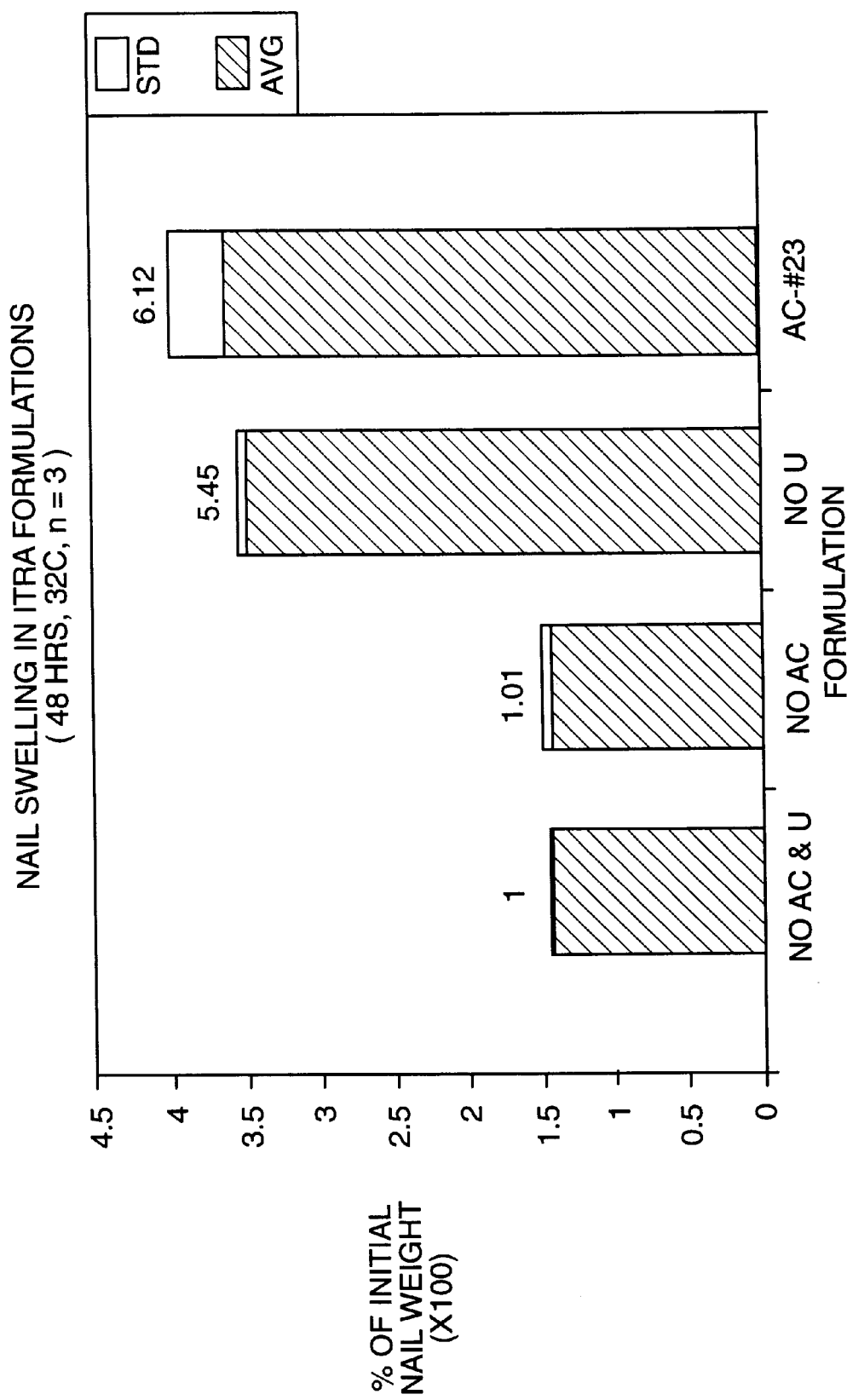
FIGS. 4a, 5a and 6a are graphs showing the effect of N-acetyl-1-cysteine and urea on nail swelling in different formulations.
Figure 4B:
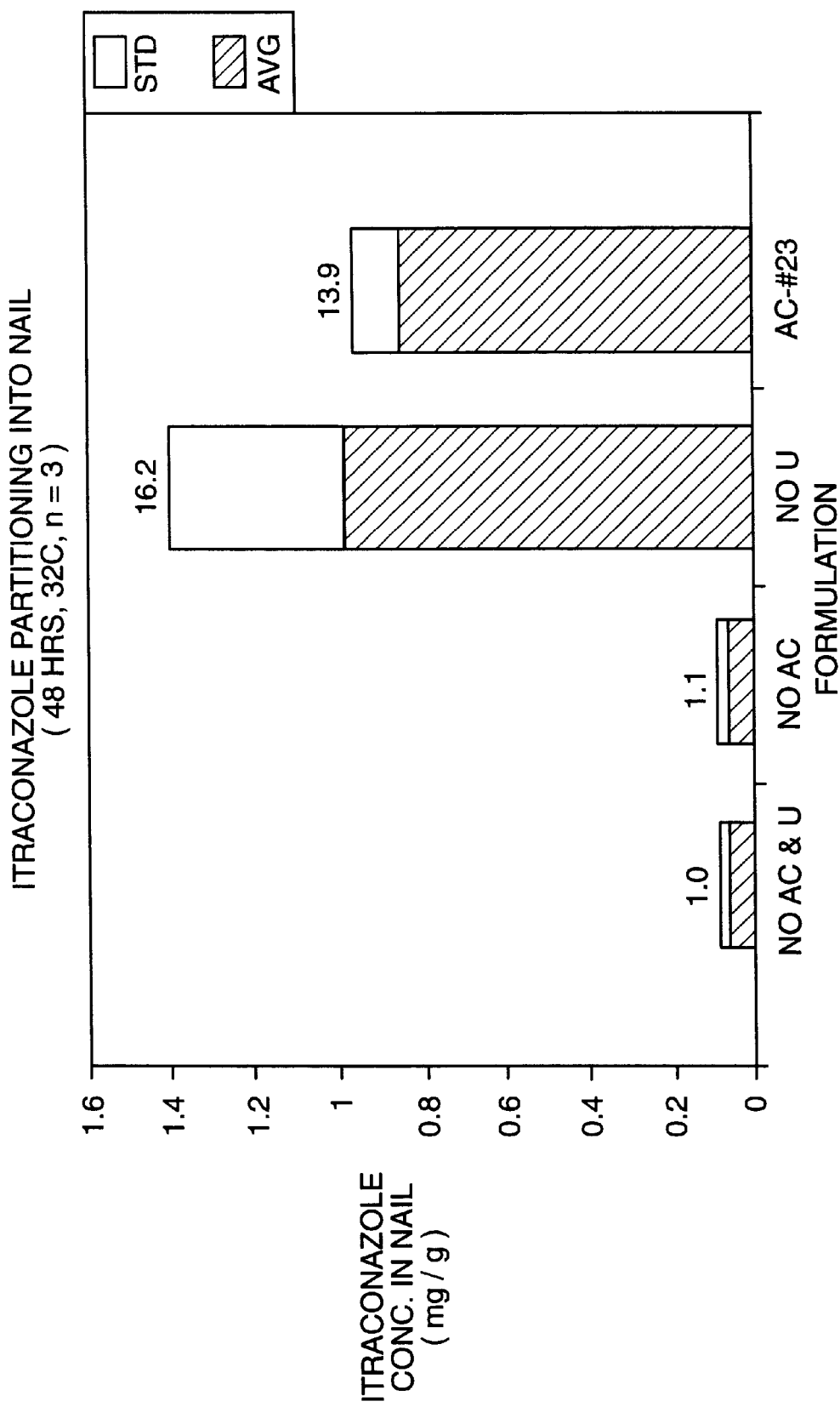
FIGS. 4b, 5b and 6b are graphs showing the effect of N-acetyl-1-cysteine and urea on itraconazole partitioning into nail in different formulations.
Figure 5A:
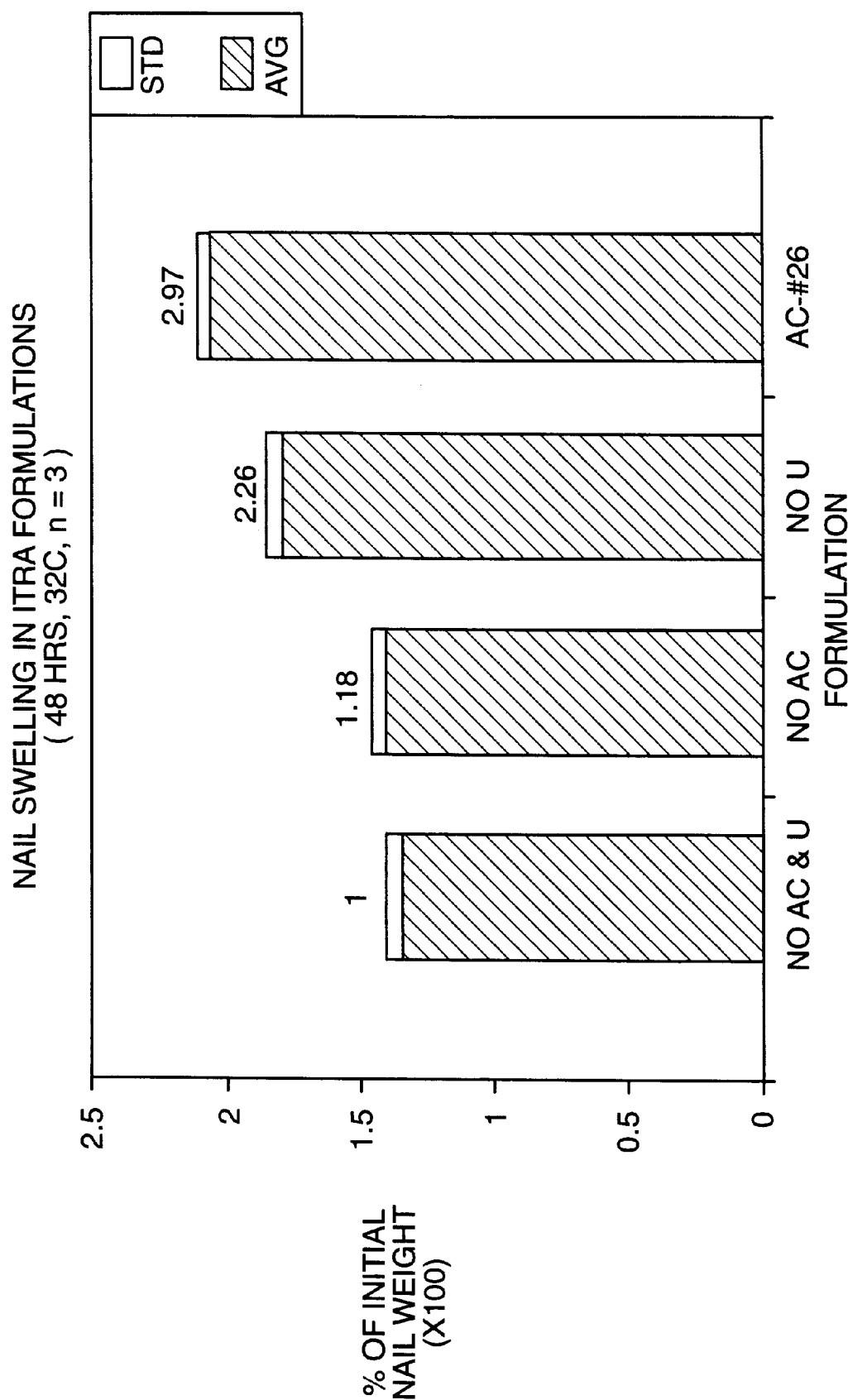
Figure 5B:
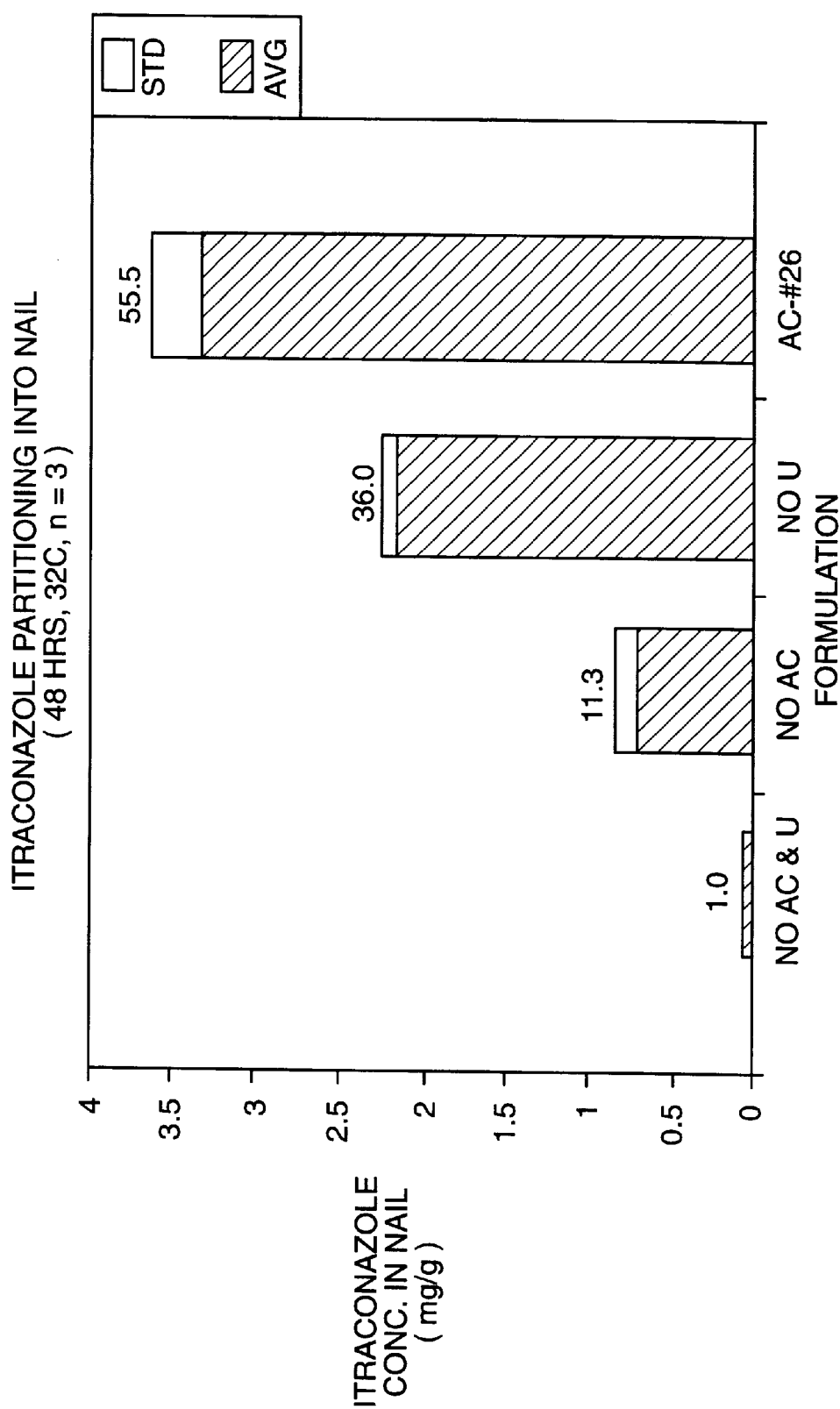
Figure 6A:
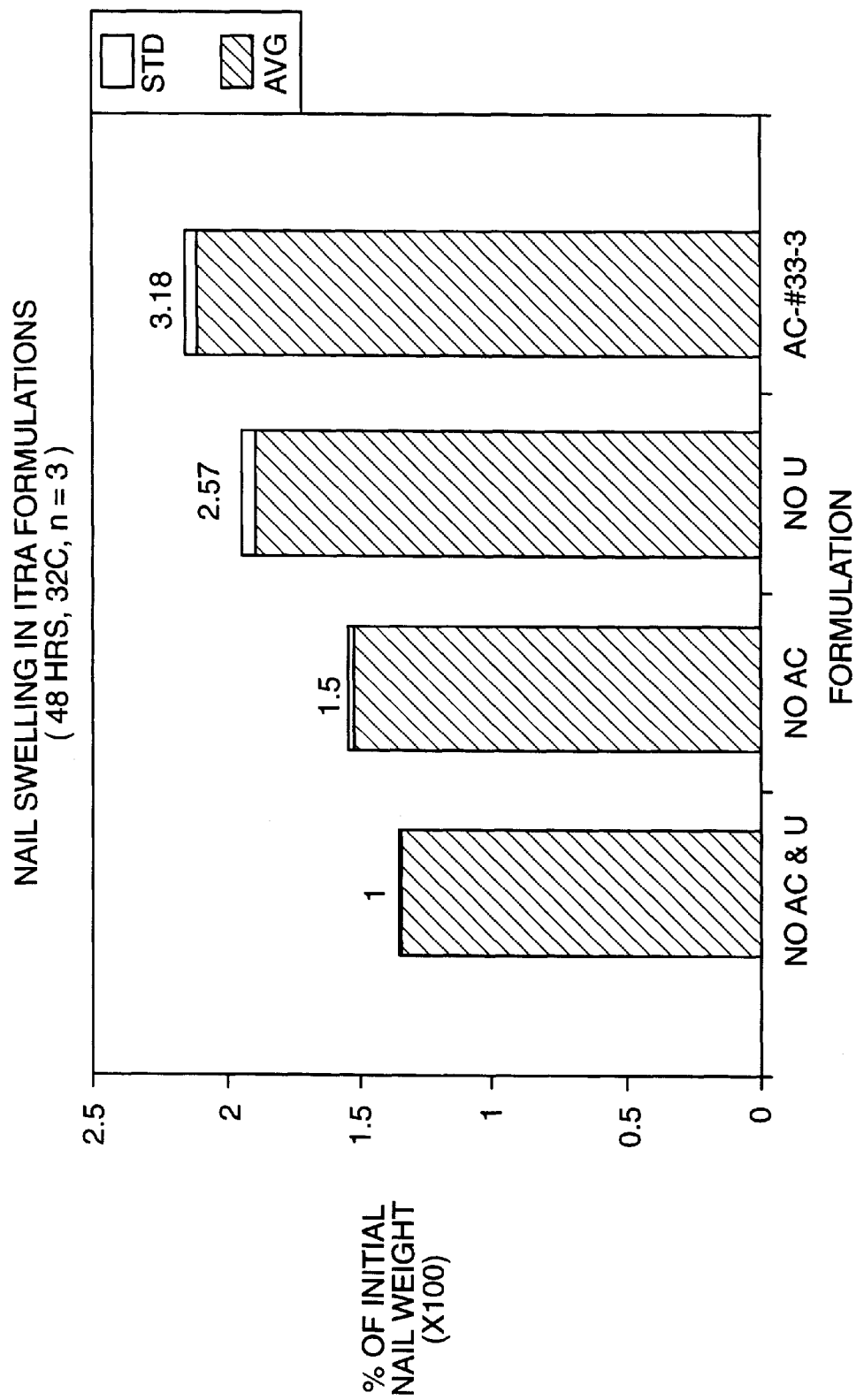
Figure 6B:
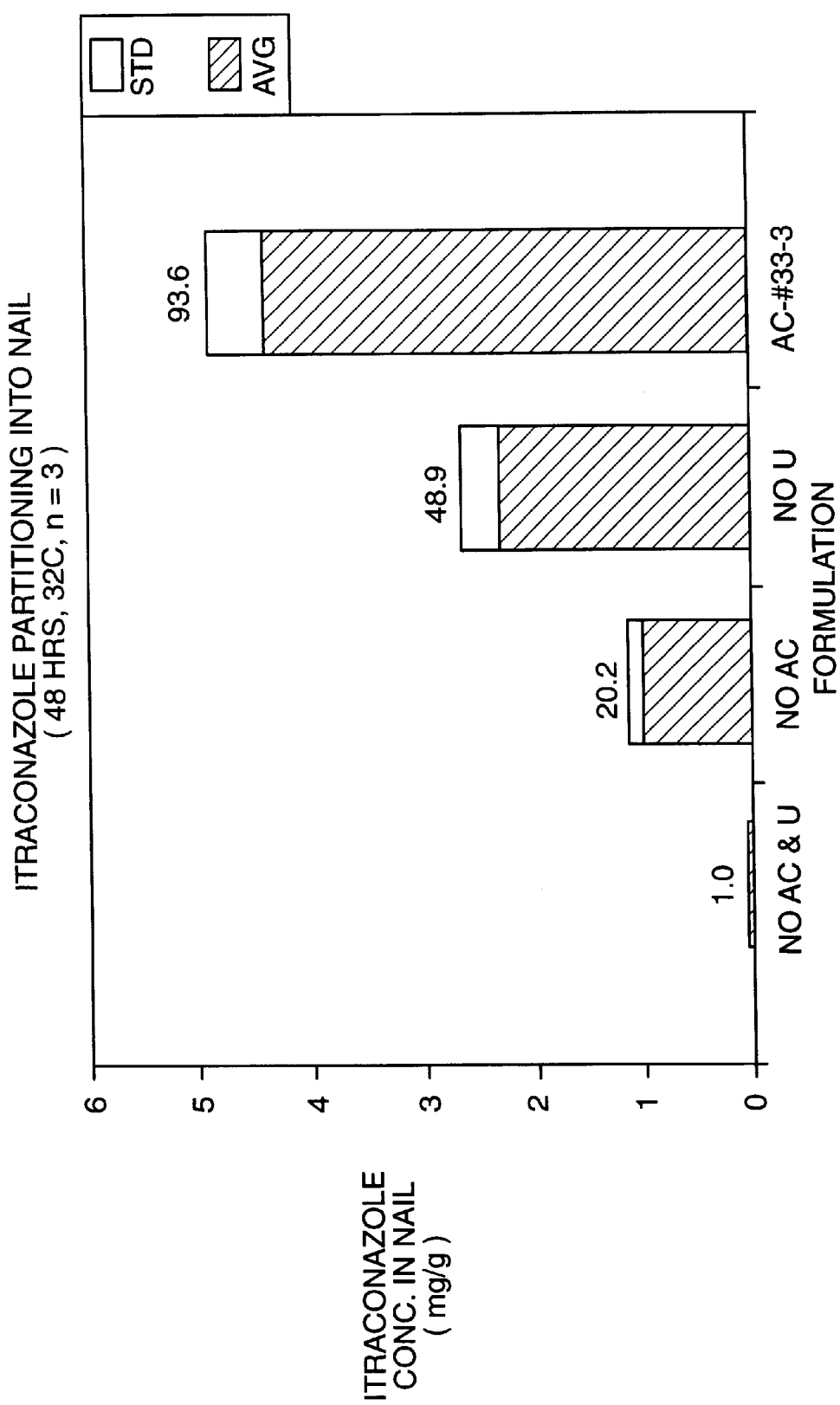

FIG. 3a shows a comparison of the nail swelling enhancement effect and FIG. 3b shows a comparison of the itraconazole partitioning enhancement effect of the thiol-containing amino acids and derivatives thereof of nail clippings after immersion in the test formulations at 32° C. for 48 hours.

The results in the FIG. 3a show that all the thiol-containing amino acid and derivatives thereof investigated increased nail swelling in the itraconazole formulations, with the enhancement factors ranging from 1.82 to 4.57. The highest nail swelling enhancement was found with 1-cysteine, followed by N-acetyl-1-cysteine and cysteamine. As shown in FIG. 3b, the same rank order was observed among the penetration enhancers for their ability in enhancing itraconazole partitioning into nail. The drastic increase in itraconazole migration into the nail (approximately 100-fold) indicates that incorporation of the penetration enhancer into a topical itraconazole formulation will definitely facilitate the antifungal drug reaching its target sites in the nail plate and the nail bed.

The graphs displayed in FIGS. 4a–6a and 4b–6b show the effect of N-acetyl-1-cysteine as penetration enhancer, and urea as adjuvant synergist on the nail swelling and itraconazole partitioning. The compositions of the formulations are tabulated in Table 3, below. All three itraconazole formulations contain 1% itraconazole, 5% N-acetyl-1-cysteine, and different concentration of urea and other components. The pH of these formulations was adjusted to 3.0. As can be seen from these figures, by adjusting the composition of a formulation, one can obtain the desired performance from the formulation, as reflected by nail swelling and itraconazole partitioning. The benefit of incorporating urea into the formulations is demonstrated by a clear trend shown in 4a–6a and 4b–6b. As can be seen, the increase of itraconazole partitioning into nail owing to the presence of urea is higher than the increase of nail swelling in all three formulations.

TABLE 3

| FORMULATIONS | | SWELLING (% wt × 100) | | | ITRA PARTITIONING (m | | |
|---|---|---|---|---|---|---|---|
| ENHANCER | | AVG | STD | Enh.F | AVG | STD | E |
| No E&U | 8054-40-5 | 1.35 | 0.01 | 1 | 0.047 | 0.011 | 1 |
| Ac Cyst | 8054-33-3 | 2.11 | 0.04 | 3.18 | 4.365 | 0.520 | 9 |
| Cysteine | 8054-34-1 | 2.59 | 0.03 | 4.57 | 4.897 | 0.149 | 1 |
| Homocyst | 8054-34-2 | 1.71 | 0.05 | 2.04 | 1.097 | 0.230 | 2 |
| Cysteam | 8054-34-3 | 2.06 | 0.01 | 3.03 | 2.632 | 0.181 | 5 |
| MethylCy | 8054-34-4 | 1.73 | 0.04 | 2.09 | 1.430 | 0.073 | 3 |
| EthylCys | 8054-34-5 | 1.64 | 0.05 | 1.82 | 1.221 | 0.213 | 2 |
| No Ac&U | 8054-40-5 | 1.43 | 0.03 | 1 | 0.061 | 0.031 | 1 |
| No Ac | 8054-40-2 | 1.43 | 0.06 | 1.01 | 0.068 | 0.031 | 1.1 |
| No U | 8054-40-3 | 3.32 | 0.23 | 5.45 | 0.990 | 0.405 | 1 |
| Ac-#23 | 8054-23 | 3.61 | 0.39 | 6.12 | 0.853 | 0.112 | 1 |
| No Ac&U | 8054-40-4 | 1.36 | 0.06 | 1 | 0.059 | 0.012 | 1 |
| No Ac | 8054-33-1 | 1.42 | 0.05 | 1.18 | 0.670 | 0.153 | 1 |
| No U | 8054-33-2 | 1.80 | 0.06 | 2.26 | 2.132 | 0.095 | 3 |
| Ac-#26 | 8054-26 | 2.06 | 0.06 | 2.97 | 3.293 | 0.303 | 5 |
| No Ac&U | 8054-40-5 | 1.35 | 0.01 | 1 | 0.047 | 0.011 | 1 |
| No Ac | 8054-33-4 | 1.52 | 0.02 | 1.5 | 0.940 | 0.167 | 2 |
| No U | 8054-33-5 | 1.90 | 0.06 | 2.57 | 2.281 | 0.339 | 4 |
| Ac-#33-3 | 8054-33-3 | 2.11 | 0.04 | 3.18 | 4.365 | 0.520 | 9 |

| | | PERMEATION | | ITRACONAZOLE IN NAIL | | | |
|---|---|---|---|---|---|---|---|
| ITRACONAZOLE NAIL PERMEATION | | (ug/cm$^2$) AVG | STD | (ug/cm$^2$) AVG | STD | (ug/cm$^{3*}$) AVG | STD |
| Repl:3d | 2138-41 | 22.28 | 8.66 | 50.31 | 20.35 | 1096.5 | 516.1 |
| Repl:1d | 2138-136 | 49.05 | 31.79 | 41.06 | 9.83 | 691.6 | 230.1 |
| Repl:1d | 2138-137 | 0.00 | 0.00 | 12.53 | 6.22 | 221.9 | 138.4 |

TABLE 3-continued

| | | PERMEATION | | MICONAZOLE NITRATE IN NAIL | | | |
|---|---|---|---|---|---|---|---|
| MICONAZOLE NITRATE NAIL PERMEATION | | ($\mu$g/cm$^2$) AVG | STD | ($\mu$g/cm$^2$) AVG | STD | ($\mu$g/cm$^3$*) AVG | STD |
| Repl:3d | 2138-69 | 4484 | 952 | 11215 | 967 | 221654 | 50389 |
| Repl:3d | 2138-70 | 1889 | 278 | 4924 | 2268 | 99384 | 59786 |
| Repl:7d | 2138-70 | 1431 | 147 | 6001 | 1371 | 99998 | 11316 |

*Calculation based on the initial volume of the untreated nail.
*$\mu$g/cm$^3$ = $\mu$g/cm$^2$ /nail thickness (cm)

A nail swelling and drug partitioning experiment was also conducted for miconazole nitrate using procedures analogous to those described above. The graphed results shown in FIG. 7 show that, similar to itraconazole data, significant nail swelling coincided with substantial miconazole partitioning into the nail, using the following formulation:

1% Miconazole nitrate, 0.005% BHA, 1.5% heavy mineral oil, 1.5% peglicol 5 oleate (LABRAFIL M 1944 CS), 10% pegoxol 7 stearate (TEFOSE 63), 0.05% EDTA, 20% urea, 10% N-acetyl-1-cysteine, and 55.9% water, with pH adjusted to 9.0 with NaOH, as required.

It should be noted that, unlike the itraconazole formulations discussed above, which were tested at pH 3, the pH value of the miconazole nitrate formulation was set at pH 9. The significant nail swelling and coinciding high miconazole-nail partitioning indicate that N-acetyl-1-cysteine has a wide working pH range. This was confirmed by the swelling-pH profile shown in FIG. 8, using the following formulation:

20% urea, 35% propylene carbonate, 10% propylene glycol, 10% N-acetyl-1-cysteine and 25% water, with pH adjusted with HCl or NaOH, as required, to pH 3.2, 4.0, 5.0, 6.0 and 7.0. The experimental temperature was 32° C.

b. Effect of Nail Penetration Enhancers on Drug Permeation Through Nail and the Drug Retention and Distribution in the Nail Plate To test the enhancement effect of N-acetyl-1-cysteine containing itraconazole formulation, itraconazole permeation experiments were conducted using human cadaver nails. Briefly, a nail plate was mounted on a nail diffusion cell (exposed nail area=0.1202 cm$^2$) in which the nail separated a donor chamber from a receptor chamber. The donor chamber was then charged with an itraconazole formulation of 100–200 mg. To simulate the clinical situation, the drug formulation in the donor chamber was removed, and replenished with fresh drug formulation according to a predetermined time schedule. The solution in the receptor chamber was 20% aqueous hydroxypropyl-β-cyclodextrin (5 ml, pH 4) to ensure sink conditions. ["Sink condition" is defined as a condition wherein the concentration of the permeant (in this case, itraconazole) in the receptor solution is lower than 10% of its solubility in the receptor solution— the idea is to drive the equilibrium such that the permeation of the permeant into the receptor solution is favored.] The experiments were run under occlusive conditions (i.e., the donor compartment was covered with a PVC film to minimize evaporation and to exclude the atmospheric oxygen) and at 32° C. With a predetermined sampling schedule, an aliquot of receptor solution was removed for itraconazole HPLC assay, and was replaced with an equal volume of fresh receptor medium. A typical nail permeation experiment ran for about 4 weeks. At the end of the permeation experiment, the itraconazole content in the nail plate was also determined by HPLC after the extraction procedure cited above (Badcock and Davies). Similar experiments were also conducted for miconazole nitrate nail permeation.

Figure 9:
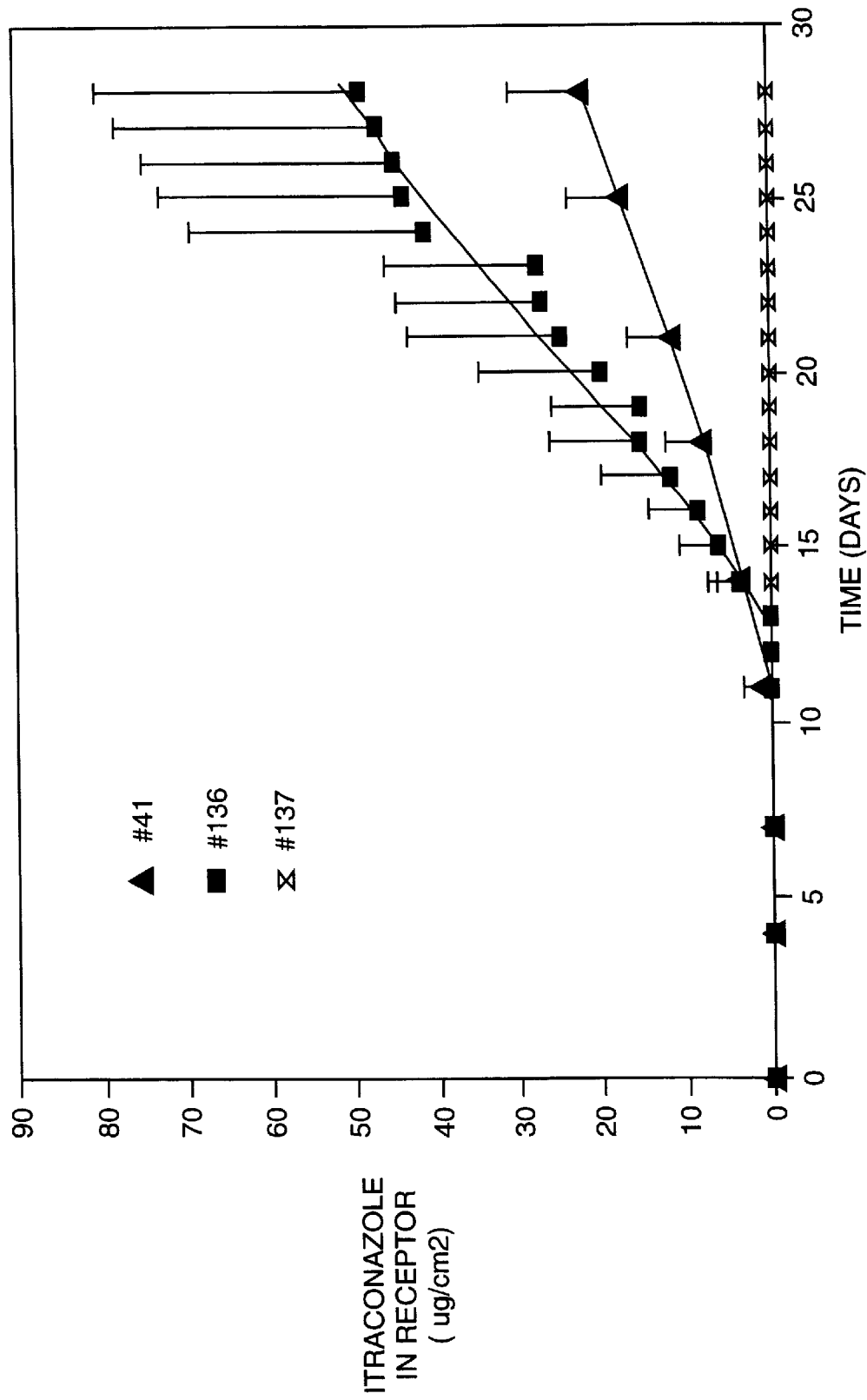
FIG. 9 is a graph showing the permeation profiles of itraconazole from three formulations with various compositions.
Figure 10:
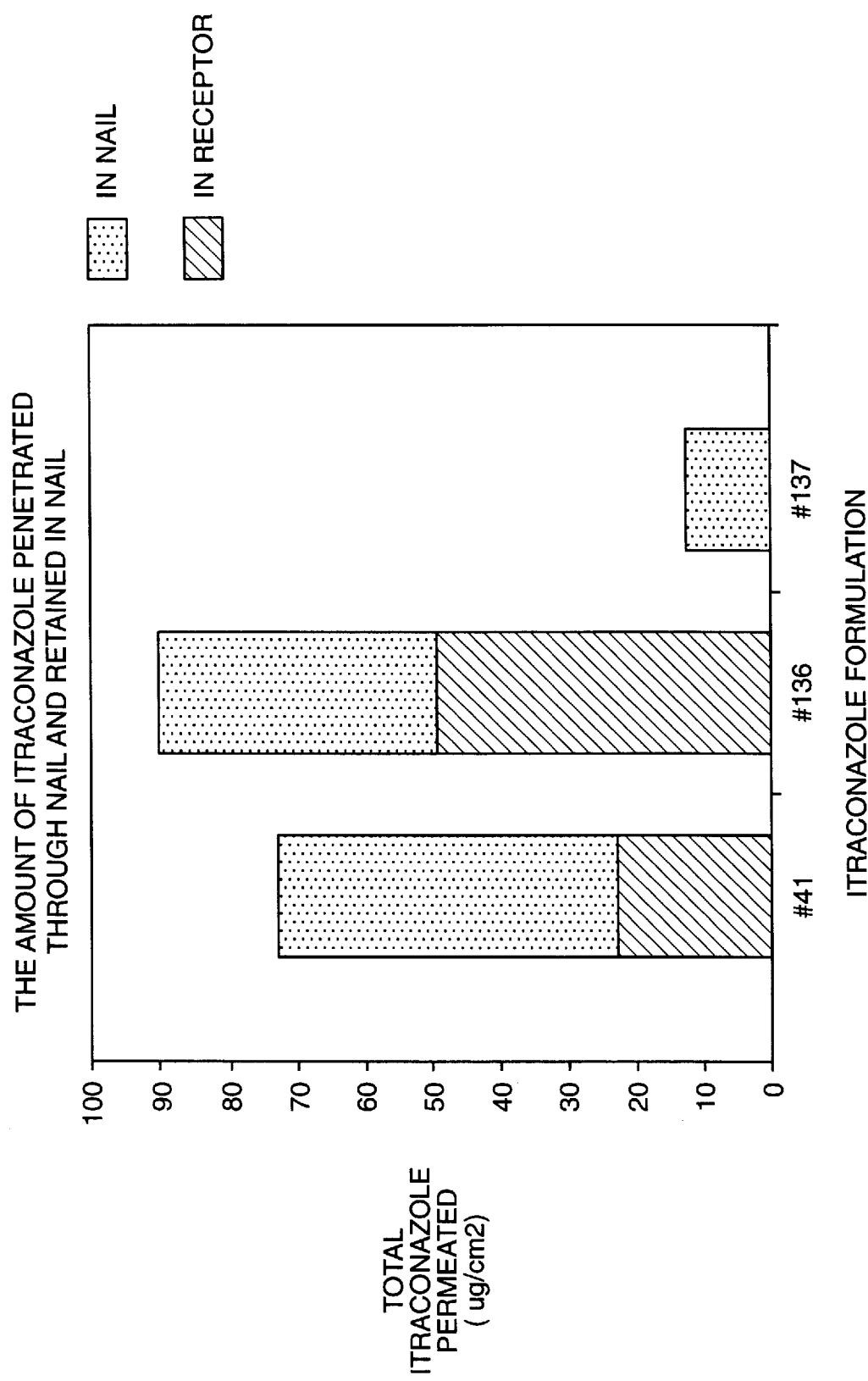
FIG. 10 is a graph showing the amount of itraconazole penetrated through the nail plate, as well as the amount retained in the nail plate, for three different formulations.

As shown in FIG. 9, the itraconazole nail permeation profiles of formulations #41 & #136 show that itraconazole started to penetrate through the nail plates to reach the receptor in approximately 12 days. The formulation #136 has an itraconazole nail permeation rate double that of formulation #41, probably due to its itraconazole content (1.0% itraconazole in #136 and 0.5% itraconazole in #41), despite the fact that formulation #41 has twice as much acetyl cysteine (10% acetyl cysteine) as formulation #136 (5% acetyl cysteine). Formulation #137 has an almost identical composition to Formulation #136, except it has a lower acetyl cysteine content (only 1.0% acetyl cysteine in #137, as opposed to 5.0% in #136). FIG. 9 shows that formulation #137 failed to deliver itraconazole across the nail plate. Apparently, the acetyl cysteine concentration in formulation #137 was too low to exert acetyl cysteine's penetration enhancing effect. FIG. 10 shows the total amount of itraconazole penetrated into the nail, including the itraconazole permeated through the nail plate, and the drug retained by the nail. The substantial amount of the drug retained in the nail reflects the highly keratinophilic nature of itraconazole. It is interesting to see that the total amount of itraconazole penetrated into the nail from formulation #137 is about ⅕ of that from formulation #136 (the same ratio as the acetyl cysteine contents of the two formulations).

It should be noted that in the in vitro experiments, the amount of itraconazole penetrated into and through the nail plate greatly exceeded the therapeutically required dose. For example (TABLE 3), formulation #2138-41 achieved an itraconazole nail concentration of 1096 $\mu$g/ml, and formulation #2138-136 achieved a concentration of 692 $\mu$g/ml. Itraconazole is a highly potent antifungal drug with a very broad spectrum of activity. The minimal inhibitory concentration (MIC) of itraconazole against both dermatophytes and yeasts is as low as 100 ng/ml.

Figure 11:
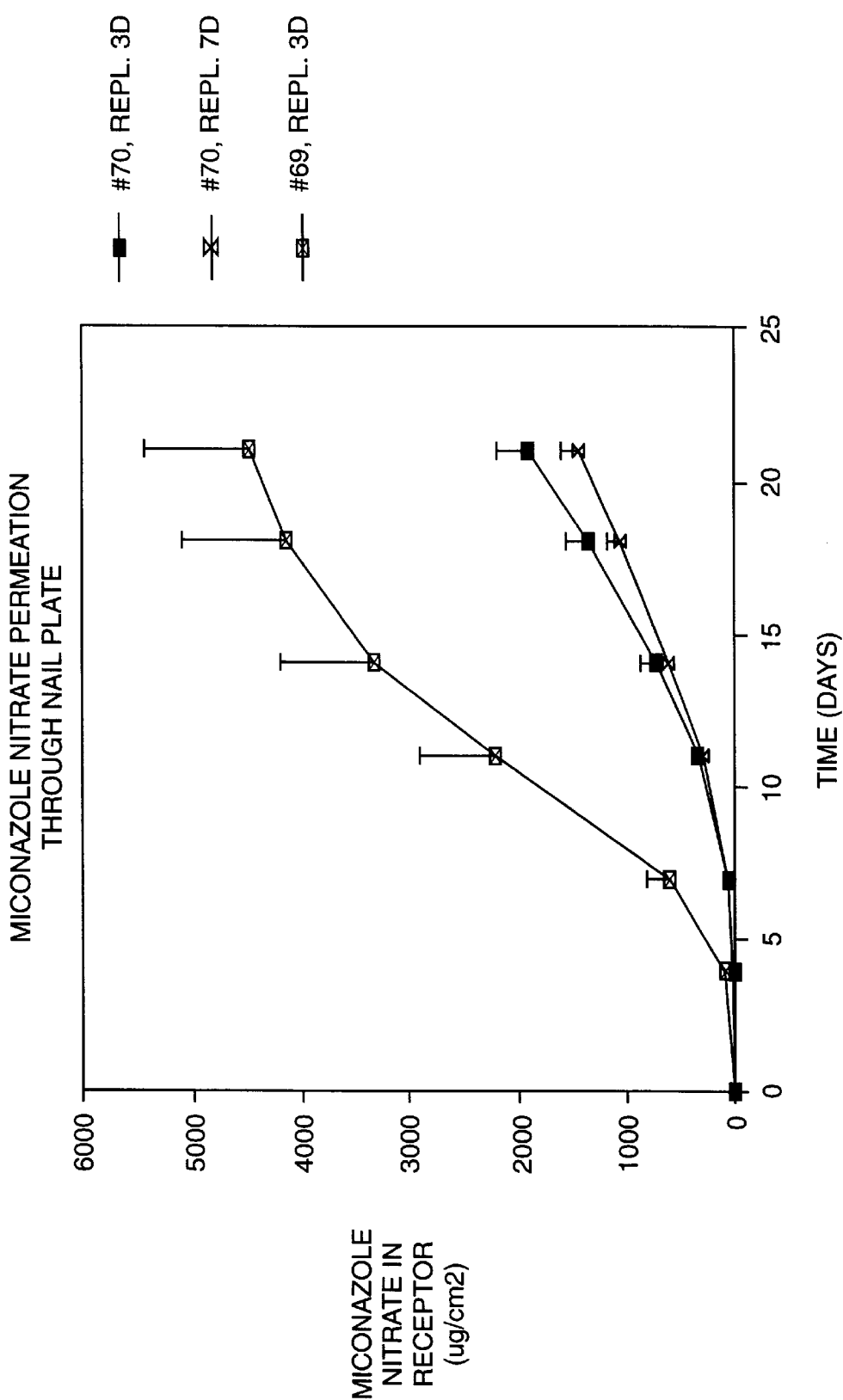
FIG. 11 is a graph showing the permeation profile of miconazole nitrate through the nail plate for three formulations.

FIG. 11 shows the permeation profile of miconazole nitrate. As can been seen, starting at day 5 (lag time=5 days), miconazole nitrate penetrated through the nail plates with a constant rate. With the same formulation, i.e., formulation #70, the frequency of replenishing the formulation (every 3 days or every 7 days) did not lead to much difference in miconazole nitrate permeation through the nail, nor in the amount of the drug retained in the nail (FIG. 12). On the other hand, when the concentration of N-acetyl-1-cysteine was increased from 5% (Formulation #70) to 10% (Formulation #69), both the miconazole nitrate permeation rate and drug retention in the nail doubled. This result indicates that the nail permeation performance of a drug formulation can be easily adjusted by choosing an appropriate penetration enhancer level. FIG. 12 shows the amount of miconazole nitrate penetrated through the nail plate, as well as the amount retained in the nail plate. The substantial amount of the drug retained in the nail reflects the keratinophilic nature of miconazole.

Stability of Itraconazole Formulation Containing N-acetyl-1-Cysteine as Nail Penetration Enhancer and Urea as Penetration Synergist An accelerated stability test on formulation #41 shows that at 99.46% of initial itraconazole in the formulation remained intact after 13 weeks in at 50° C., indicating that itraconazole in the formulation is stable enough to meet the 2-year shelf life requirement at ambient temperature.

d. Primary Dermal Irritation Test

Primary dermal irritation tests conducted on guinea pigs using two 1% itraconazole formulations (formulations #97 & #98) containing 1% and 5% acetyl cysteine, respectively. The results show that these formulations meet the requirement as topical therapeutic formulation.

e. A Specially Designed Nail Medication Delivery Device and a Two-Stage Treatment Regimen for Topical Antifungal Therapy Because sulfhydryl compounds are highly oxidizable by the oxygen in the air, the stability of a sulfhydryl nail penetration enhancer during storage presents a problem. For this reason, an antifungal formulation containing the sulfhydryl penetration enhancer are preferably applied to the nail in a specially designed nail medication delivery device in order to maintain the potency of the nail penetration enhancer. The device is designed to:

(a) inhibit the sulfhydryl penetration enhancer from oxidation by oxygen in the air;

(b) provide an occlusive environment for nail swelling to take place;

(c) prevent the sensitive eponychium skin from direct contact with the sulfhydryl penetration enhancer;

(d) firmly adhere to the nail and surrounding skin with desired contour and pliability; and (e) be convenient for patients to use.

Urea tends to undergo a biuret reaction during storage, which could cause a pH shift in the formulation. Since the solubility of some antifungal drugs such as itraconazole decreases as the formulation pH increases, the pH shift would significantly reduce the dissolved form of itraconazole available for penetration, thereby reducing its therapeutic efficacy. The stability problem of the sulfhydryl nail penetration enhancer during storage and application, and the pH shifting problem due to urea, may be resolved by using a nail medication delivery device designed as described below. The nail medication delivery device comprises a bandage adapted for the topical administration of medication to the nail, said bandage comprising a T-shaped adhesive backing, and a flexible pad having an impervious backing and a nail-shaped cavity, wherein said nail-shaped cavity contains absorptive means having absorbed therein urea and sulfhydryl penetration enhancer, both of said compounds being in a water-free condition. That is, the absorptive means is sufficiently free of water that the urea and sulfhydryl penetration enhancer remain stable under ordinary storage conditions (at 25° C.) for a reasonable shelf life period of, e.g., at least six to twelve months.

Figure 13A:
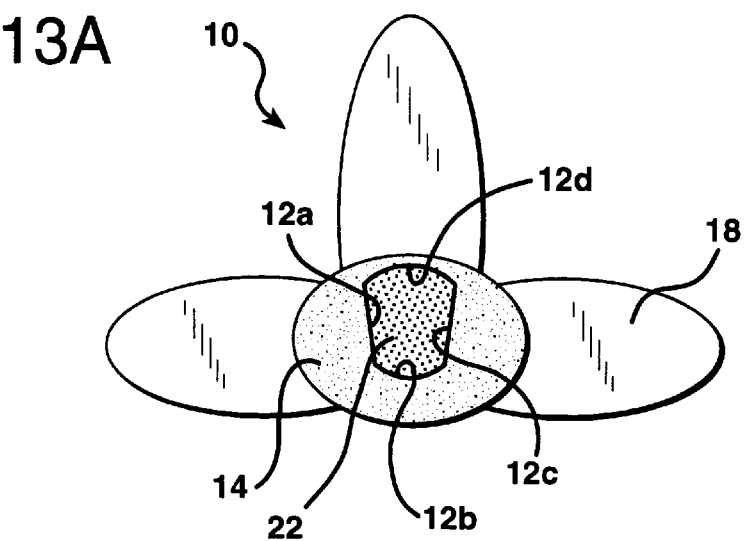
FIG. 13 shows three views of a device designed for topical drug delivery to nails.
Figure 13B:
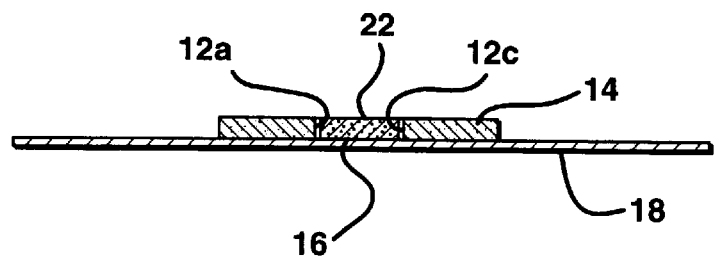
Figure 13C:
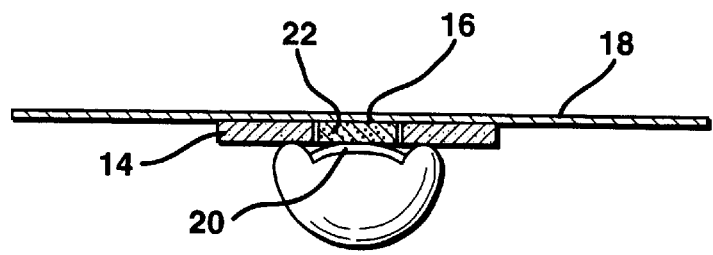

This nail medication delivery device includes dehydrated sulfhydryl penetration enhancer and urea in its structure, separate from the antifungal drug formulation, hence greatly reducing the instability problem. FIG. 13 shows the nail medication delivery device 10. The device includes a pliable polyethylene closed-cell foam pad 14 (the pad 14 is preferably adhesive-coated on the surface that will be in contact with the finger or toe whose nail is being treated) that includes a nail shaped cavity or well defined by walls 12 a–d and an impervious backing 16 (which can be a portion of the adhesive backing 18). The well contains a nonwoven pad or a lyophilized porous layer 22 that contains a predetermined amount of sulfhydryl nail penetration enhancer and urea. (In lieu of the pad or layer 22, other conventional absorption means for storing the urea and sulfhydryl nail penetration enhancer may be used.) This pad or layer 22 serves as a drug reservoir. The impervious backing 16 helps to keep moisture in and oxygen out. The adhesive backing 18 is arranged to form a T-shaped bandage 10, which secures the drug formulation-containing nail medication delivery device 10 on a finger tip or toe 20. The nail medication delivery device 10 is preferably stored in a metallic laminate blister package (not shown), which may be filled with an inert gas such as $N_2$ or argon, to help ensure the shelf-life of the urea and sulfhydryl nail penetration enhancer. During a clinical application, a stable itraconazole formulation containing no sulfhydryl penetration enhancer and urea, and packaged in a conventional tube, is charged into the drug reservoir 22 of the device by application to the surface of the nonwoven pad or a lyophilized porous layer (or other absorption means). N-acetyl-1-cysteine [or other compound of Formula (I)] and urea immediately dissolve in the drug formulation, and exert their penetration enhancing effect to the nail 20, when applied to the nail during treatment. Another advantage of the enhancer-containing nail device is its universal usefulness for any antifungal drug formulation.

Because the combination of sulfhydryl nail penetration enhancer and urea has a prolonged enhancement effect on the nail permeability for the antifungal drug, a two-stage antifungal treatment regimen may be employed. The first stage consists of an initial treatment period (e.g., 1–3 weeks) with a topical antifungal formulation and a nail drug delivery device, which contains both sulfhydryl penetration enhancer and urea. As discussed above, the nail medication delivery device is designed in such a way that it provides occlusive conditions, that is, oxygen exclusion to enhance the stability of the nail penetration enhancer, and moisture retention to maximize the water content of the nail, thereby to promote high drug penetration. By the end of the first stage treatment, nail permeability to the antifungal drug has been increased significantly, and a sufficient amount of antifungal drug has reached the targeted sites (i.e., nail plate, nail bed and nail matrix) to exert antifungal action. The strong binding between certain antifungal drugs (e.g., itraconazole and miconazole) and nail keratin will likely result in a drug concentration in nail significantly above its therapeutic level for a long time. The second stage of the treatment is a maintenance therapy involving periodic applications of antifungal formulation without the penetration enhancer and urea. (This is possible because the urea acts to prevent the keratin from returning to its original densely packed cross-linked state, thereby maintaining the permeability of the nail to the antifungal drug formulation.) The simplified procedure of the maintenance stage is user-friendly, and will help encourage long-term compliance by patients.

The following are representative formulations of antifungal drug, penetration enhancer and urea that are suitable for use in the invention:

| FORMULATION A | w/w % |
|---|---|
| Miconazole nitrate | 2.0% |
| Propylene carbonate | 35.0% |
| Propylene glycol | 10.0% |
| EDTA | 0.1% |
| Urea | 20.0% |
| 1-Cysteine | 10.0% |
| Purified water | 22.9% |
| Adjust pH to 8.00 with aq. 50% NaOH | |

Note: Formulations containing miconazole nitrate can have pH values of from about 3 to about 9.

| FORMULATION B (pH 8) | w/w % |
|---|---|
| Miconazole nitrate | 1.0% |
| Propylene carbonate | 20.0% |
| Propylene glycol | 10.0% |
| EDTA | 0.1% |
| Urea | 20.0% |
| 1-Cysteine | 10.0% |
| Isopropyl alcohol | 10.0% |
| Adjust pH to 8.00 with aq. 50% NaOH | |
| QS with distilled water to 100% | (approx. 28%) |

| FORMULATION C (pH 9) | (w/w %) |
|---|---|
| Miconazole nitrate | 1.0% |
| Propylene carbonate | 20.0% |
| Propylene glycol | 10.0% |
| EDTA | 0.1% |
| Urea | 20.0% |
| 1-Cysteine | 10.0% |
| Isopropyl alcohol | 10.0% |
| Adjust pH to 9.00 with aq. 50% NaOH | |
| QS with distilled water to 100% | (approx. 28%) |

| FORMULATION D (pH 8) | (w/w %) |
|---|---|
| Miconazole nitrate | 1.0% |
| Propylene carbonate | 20.0% |
| Propylene glycol | 10.0% |
| EDTA | 0.1% |
| Urea | 20.0% |
| N-acetyl-1-cysteine | 10.0% |
| Isopropyl alcohol | 10.0% |
| Adjust pH to 8.00 with 50% aq. NaOH | |
| QS with distilled water to 100% | (approx. 28%) |

| FORMULATION E (pH 9) | (w/w %) |
|---|---|
| Miconazole nitrate | 1.0% |
| Propylene carbonate | 20.0% |
| Propylene glycol | 10.0% |
| EDTA | 0.1% |
| Urea | 20.0% |
| N-acetyl-1-cysteine | 10.0% |
| Isopropyl alcohol | 10.0% |
| Adjust pH to 9.00 with 50% aq. NaOH | |
| QS with distilled water to 100% | (approx. 28%) |

| FORMULATION F (CREAM) | w/w % |
|---|---|
| BHA, NF | 0.01% |
| Miconazole nitrate, USP | 2.00% |
| Mineral oil, USP (heavy) | 3.00% |
| Peglicol 5 Oleate (LABRAFIL M 1944 CS) | 3.00% |
| Pegoxol 7 stearate (TEFOSE 63) | 20.00% |
| EDTA | 0.10% |
| Urea | 20.00% |
| N-acetyl-1-cysteine | 10.00% |
| Adjust to pH 8.00 with 50% aq. NaOH | |
| QS with Purified water (USP) to 100% | (approx. 40%) |

The following is a formulation of antifungal drug suitable for use after the nail has been treated with penetration enhancer and urea, as described above.

| FORMULATION G (CREAM) | w/w % |
|---|---|
| Benzoic acid, USP | 0.2000% |
| BHA, NF | 0.0052% |
| Miconazole nitrate, USP | 2.0000% |
| Mineral oil, USP (heavy) | 3.0000% |
| Peglicol 5 Oleate (LABRAFIL M 1944 CS) | 3.0000% |
| Pegoxol 7 stearate (TEFOSE 63) | 20.0000% |
| Purified water, USP | 71.7948% |
| pH 3–4 | |

The following are preferred formulations containing itraconazole:

| FORMULATION H (pH 3) | w/w % |
|---|---|
| Itraconazole | 1.0% |
| Propylene carbonate | 35.0% |
| Propylene glycol | 16.5% |
| EDTA | 0.1% |
| Urea | 10.0% |
| N-acetyl-1-cysteine | 5.0% |
| Salicylic acid | 5.0% |
| BHT | 0.05% |
| Adjust pH to 3.0 with 1 N NaOH | |
| QS with distilled water to 100% | (approx. 25%) |

Note: Formulations containing itraconazole preferably have a relatively low pH, such as from about pH 2 to pH 4, in order to enhance the solubility of itraconazole in the formulation.

| FORMULATION I (pH 3) | w/w % |
|---|---|
| Itraconazole | 1.0% |
| Propylene carbonate | 35.0% |
| Propylene glycol | 14.0% |
| EDTA | 0.1% |
| Urea | 10.0% |
| N-acetyl-1-cysteine | 5.0% |
| Salicylic acid | 5.0% |
| BHT | 0.05% |
| Adjust pH to 3.0 with 1 N NaOH | |
| QS with distilled water to 100% | (approx. 27.5%) |

| FORMULATION J (pH 3) | w/w % |
|---|---|
| Itraconazole | 1.0% |
| propylene carbonate | 35.0% |
| Propylene glycol | 10.0% |
| Urea | 10.0% |
| Acetylcysteine | 5.0% |
| Disodium EDTA | 0.1% |
| BHT | 0.1% |
| Klucel | 2.0% |
| pH adjusted to 3 with 0.1N HCl | |
| Water Q.S. | 100.00% |

| FORMULATION K (pH 3) | w/w % |
|---|---|
| Itraconazole | 1.0% |
| Propylene carbonate | 35.0% |
| Propylene glycol | 10.0% |
| Urea | 20.0% |
| Acetylcysteine | 5.0% |
| Disodium EDTA | 0.1% |
| BHT | 0.1% |
| Klucel | 2.0% |
| pH adjusted to 3 with 0.1N HCl | |
| Water Q.S. | 100.00% |

| FORMULATION L | Weight |
|---|---|
| Itraconazole | 50 mg |
| Propylene carbonate | 350 mg |
| Propylene glycol | 100 mg |
| Urea | 200 mg |
| N-Acetyl-1-cysteine | 50 mg |
| Hydroxypropyl cellulose | 20 mg |
| EDTA (Na salt) | 1 mg |
| BHT | 0.5 mg |
| Conc. HCl q.s. to pH 3 | |
| Purified water q.s. ad | 1000 mg |

Formulations containing from about 10 to 50% (by weight) propylene carbonate (4-methyl-1,3-dioxolan-2-one) and about 5 to 30% propylene glycol are desirable because itraconazole and other anti-fungal compounds that have low solubility in water are soluble in such formulations. These compounds also help to enhance penetration of the antifungal drug into the nail.

Treatment Trials with Volunteers:

1: A 57 year old female had onychomycosis of the left thumb nail for approximately 20 years. The involved nail plate had a characteristic groovy uneven surface. A topical formulation containing 1% Itraconazole, 5% acetyl cysteine, 10% urea and other pharmaceutical excipients (similar to Formulation H) was applied to the nail, under occluded conditions, daily for seven days. At the same time a similar formulation, but without acetyl cysteine, was applied to the skin surrounding the nail. A six-month follow-up showed the nail to be clinically cured. The newly grown nail had a healthy normal appearance.

2: A 32 year old female had onychomycosis of both big toe nails for approximately 8 years. The involved nails had significantly thickened nail plates and dark gray color. A topical formulation containing 1% Itraconazole, 5% acetyl cysteine, 10% urea and other pharmaceutical excipients (similar to Formulation J) was applied to the nail, under occluded conditions, daily for seven days. Following the initial treatment, a similar formulation, but without acetyl cysteine, was applied to the nail under occlusion for two more weeks. A six-month follow-up showed the nails to be clinically improved. The newly grown nails returned to the normal thickness, and the gray area of the nails were significantly reduced.

What is claimed is:

1. A method for the treatment of fungal diseases in nails, which comprises the topical administration to the affected nail, or to the affected nail and surrounding skin:

(1) a compound represented by Formula (I):

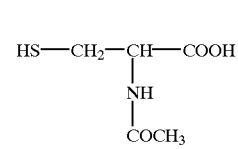

and (2) an effective amount of an antifungal drug is selected from the group consisting of itraconazole, pharmaceutically acceptable salts thereof and stereoisomers thereof, (1) being administered in an amount sufficient to enhance the permeation of said antifungal drug through nail tissue, and (1) and (2) being administered either prior to or concurrently with the topical administration to the nail of said antifungal drug and the composition is substantially free of urea.

2. The method of claim 1 wherein the N-acetyl-1-cysteine and antifungal drug are administered to the nail under occlusive conditions.

3. A bandage adapted for the topical administration of medication to the nail, said bandage comprising a T-shaped adhesive backing, and a flexible pad having an impervious backing and a nail-shaped cavity backed by said impervious backing, wherein said nail-shaped cavity contains absorptive means having absorbed therein N-acetyl-1-cysteine and an antifungal drug selected from the group consisting of itraconazole, pharmaceutically-acceptable salts of itraconazole and stereoisomers of itraconazole.

4. A composition comprising N-acetyl-1-cysteine, an antifungal drug selected from the group consisting of itraconazole, pharmaceutically-acceptable salts of itraconazole and stereoisomers of itraconazole, said N-acetyl-1-cysteine and said antifungal drug being present in an amount sufficient to enhance the permeation of said antifungal drug through nail tissue and said composition being substantially free of urea.

5. A composition according to claim 4 wherein said composition contains propylene carbonate and propylene glycol.

* * * * *